US009198985B2

(12) United States Patent
Adkins et al.

(10) Patent No.: US 9,198,985 B2
(45) Date of Patent: Dec. 1, 2015

(54) BIMODAL STAR POLYMER ARCHITECTURES AS FLUORESCENT AND MRI IMAGING REAGENTS

(75) Inventors: Chinessa T. Adkins, Nashville, TN (US); Eva M. Harth, Nashville, TN (US)

(73) Assignee: Vanderbuilt University, Nashville, TN (US)

( * ) Notice: Subject to any disclaimer, the term of this patent is extended or adjusted under 35 U.S.C. 154(b) by 611 days.

(21) Appl. No.: 13/321,897

(22) PCT Filed: May 21, 2010
(Under 37 CFR 1.47)

(86) PCT No.: PCT/US2010/035808
§ 371 (c)(1),
(2), (4) Date: Jun. 8, 2012

(87) PCT Pub. No.: WO2010/135666
PCT Pub. Date: Nov. 25, 2010

(65) Prior Publication Data
US 2013/0029369 A1   Jan. 31, 2013

Related U.S. Application Data

(60) Provisional application No. 61/180,479, filed on May 22, 2009.

(51) Int. Cl.
*C12Q 1/02* (2006.01)
*A61K 49/00* (2006.01)
*C08G 83/00* (2006.01)

(52) U.S. Cl.
CPC .......... *A61K 49/0002* (2013.01); *A61K 49/0021* (2013.01); *A61K 49/0054* (2013.01); *C08G 83/003* (2013.01)

(58) Field of Classification Search
CPC ........... A61K 49/0002; A61K 49/0054; A61K 49/0021; C08G 83/003
See application file for complete search history.

(56) References Cited

U.S. PATENT DOCUMENTS

| | | | |
|---|---|---|---|
| 5,182,316 A | 1/1993 | De Voe et al. | 522/99 |
| 5,527,524 A | 6/1996 | Tomalia et al. | 424/78.17 |
| 6,350,431 B1 | 2/2002 | Snow et al. | 424/9.6 |
| 2004/0223909 A1 | 11/2004 | Montalto et al. | 424/9.1 |
| 2005/0009109 A1 | 1/2005 | Moerner et al. | 435/7.2 |

FOREIGN PATENT DOCUMENTS

WO   PCT/US2010/035808   5/2010

OTHER PUBLICATIONS

Grabchev et al. Polymer (2007) 6755-6762.*
Atkins et al. Polymeric Materials: Science and Engineering (2007) 97: 61.*
Zheng et al. Polymer Preprints (2007) 48(2): 1044-1045.*
International Search Report issued Jul. 29, 2010 by the International Searching Authority for Application No. PCT/US2010/035808 filed May 21,2010 and later published as WO 2010/135666 on Nov. 25, 2010 (Applicant—Vanderbilt University // Inventor—Adkins, et al.) (2 pages).
Written Opinion issued Jul. 29, 2010 by the International Searching Authority for Application No. PCT/US2010/035808 filed May 21, 2010 and later published as WO 2010/135666 on Nov. 25, 2010 (Applicant—Vanderbilt University // Inventor—Adkins, et al.) (6 pages).
International Preliminary Report on Patentability issued Nov. 22, 2011 by the International Searching Authority for Application No. PCT/US2010/035808 filed May 21, 2010 and later published as WO 2010/135666 on Nov. 25, 2010 (Applicant—Vanderbilt University // Inventor—Adkins, et al.) (7 pages).
Adkins, et al., "Synthesis of star polymer architectures with site isolated chromophores," *Macromolecules*, 2008, 41(10): pp. 3472-3480.
Allen, et al. "Contrast agents for magnetic resonance imaging synthesized with ring-opening metathesis polymerization," *J. Am. Chem. Soc.*, 2006, 128(20): pp. 6534-6535.
Ghoroghchian et al. "Near infrared-emissive polymersomes: a self-assembled soft matter for in vivo optical imaging," *PNAS*, 2005, 102(8): pp. 2922-2927.
Moulay, et al. "Hydroquinone/catechol-bearing polyacrylic and redox polymer," *Reactive and Functional Polymer*, 2004, 61(2): pp. 265-275.
Talanov, et al., "Dendrimer-based nanoprobe for dual modality magnetic resonance and fluorescence imaging," *Nano Letters*, 2006, 6(7): pp. 1459-1463.

* cited by examiner

*Primary Examiner* — Susan Hanley
(74) *Attorney, Agent, or Firm* — Ballard Spahr LLP

(57) ABSTRACT

Disclosed are star polymers comprising a polymeric body having a core with a site-isolated chromophore and a plurality of polymer chains emanating from the core; and at least one chelating moiety bonded to at least one polymer chain. Also disclosed are bimodal contrast agents derived from star polymers and further comprising at least one metal chelated by the at least one chelating moiety. Also disclosed are methods of making and using same. Also disclosed are imaging methods employing the disclosed star polymers and/or bimodal contrast agents. This abstract is intended as a scanning tool for purposes of searching in the particular art and is not intended to be limiting of the present invention.

10 Claims, 14 Drawing Sheets a (i) vinyltrimethylsilane, Pd(OAc)2, PPh3, Et3N, dimethylformamide, 100°C; (ii) n-Bu4NF/tetrahydrofuran, 90°C.

BIMODAL STAR POLYMER ARCHITECTURES AS FLUORESCENT AND MRI IMAGING REAGENTS

CROSS-REFERENCE TO RELATED APPLICATIONS

This application claims the benefit of U.S. Application No. 61/180,479, filed May 22, 2009; which is hereby incorporated herein by reference in entirety.

ACKNOWLEDGMENT

This invention was made with government support under ACS PRF Grant No. 46620-G7, awarded by the American Chemical Society; under CAREER Grant CHE-0645737, awarded by the National Science Foundation; and under Chemistry-Biology Interface Program Fellowship Training Grant No. T32 GM065086-5, awarded by the National Institutes of Health. The United States government has certain rights in the invention.

BACKGROUND

In recent years there has been a significant increase in the development of procedures that combine architectural control with flexibility in the incorporation of functional groups due to the increasing demand for functionalized soft materials. Well-defined three-dimensional structures such as microgels, star polymers, micelles, and dendrimers have been explored because they are considered to be building blocks for a variety of nanotechnology applications that take advantage of the high number of functional groups. In particular, star polymers, which are composed of multiple polymer chains emanating from a central core, have advantages due to their compact structure and synthetic ease of preparation. Likewise, analytical technologies have developed that allow in vivo imaging of cells and tissue structures. For example, fluorescence detection and magnetic resonance imaging (MRI) allow for imaging of microstructures within subjects with a high degree of resolution.

Conventional techniques, however, fail to provide water-soluble, well-defined, three-dimensional nanostructures capable of cell membrane transport and imaging by more than one detection method. Further, conventional techniques fail to provide satisfactory contrast for imaging by MRI. There deficiencies and other deficiencies are remedied by the disclosed compositions and methods.

SUMMARY

In accordance with the purpose(s) of the invention, as embodied and broadly described herein, the invention, in one aspect, relates to star polymers bearing one or more chelating moieties and bimodal contrast agents derived therefrom.

Disclosed are bimodal contrast agents comprising a polymeric body having a core and a plurality of polymer chains emanating from the core; at least one chromophore within the body; at least one chelating moiety bonded to at least one polymer chain; and at least one metal chelated by the at least one chelating moiety.

Also disclosed are star polymers comprising a polymeric body having a core with a site-isolated chromophore and a plurality of polymer chains emanating from the core; and at least one chelating moiety bonded to at least one polymer chain.

Also disclosed are methods of making a star polymer comprising the step of introducing at least one chelating moiety into the polymer.

Also disclosed are methods of making a bimodal contrast agent comprising the steps of providing a star polymer comprising a polymeric body having a core with a site-isolated chromophore and a plurality of polymer chains emanating from the core; and at least one chelating moiety bonded to at least one polymer chain, and chelating at least one metal with the at least one chelating moiety.

Also disclosed are the products of the disclosed methods of making.

Also disclosed are imaging methods comprising the steps of administering into a cell a diagnostically effective amount of a bimodal contrast agent comprising a polymeric body having a core and a plurality of polymer chains emanating from the core; at least one chromophore within the body; at least one chelating moiety bonded to at least one polymer chain; and at least one metal chelated by the at least one chelating moiety, and imaging the cell with one or both of a Magnetic Resonance Imaging apparatus or a chromatographic detector.

Also disclosed are imaging methods comprising the steps of administering into soft tissue of a subject a diagnostically effective amount of a bimodal contrast agent comprising a polymeric body having a core and a plurality of polymer chains emanating from the core; at least one chromophore within the body; at least one chelating moiety bonded to at least one polymer chain; and at least one metal chelated by the at least one chelating moiety, and imaging the soft tissue of the subject with one or both of a Magnetic Resonance Imaging apparatus or a chromatographic detector.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
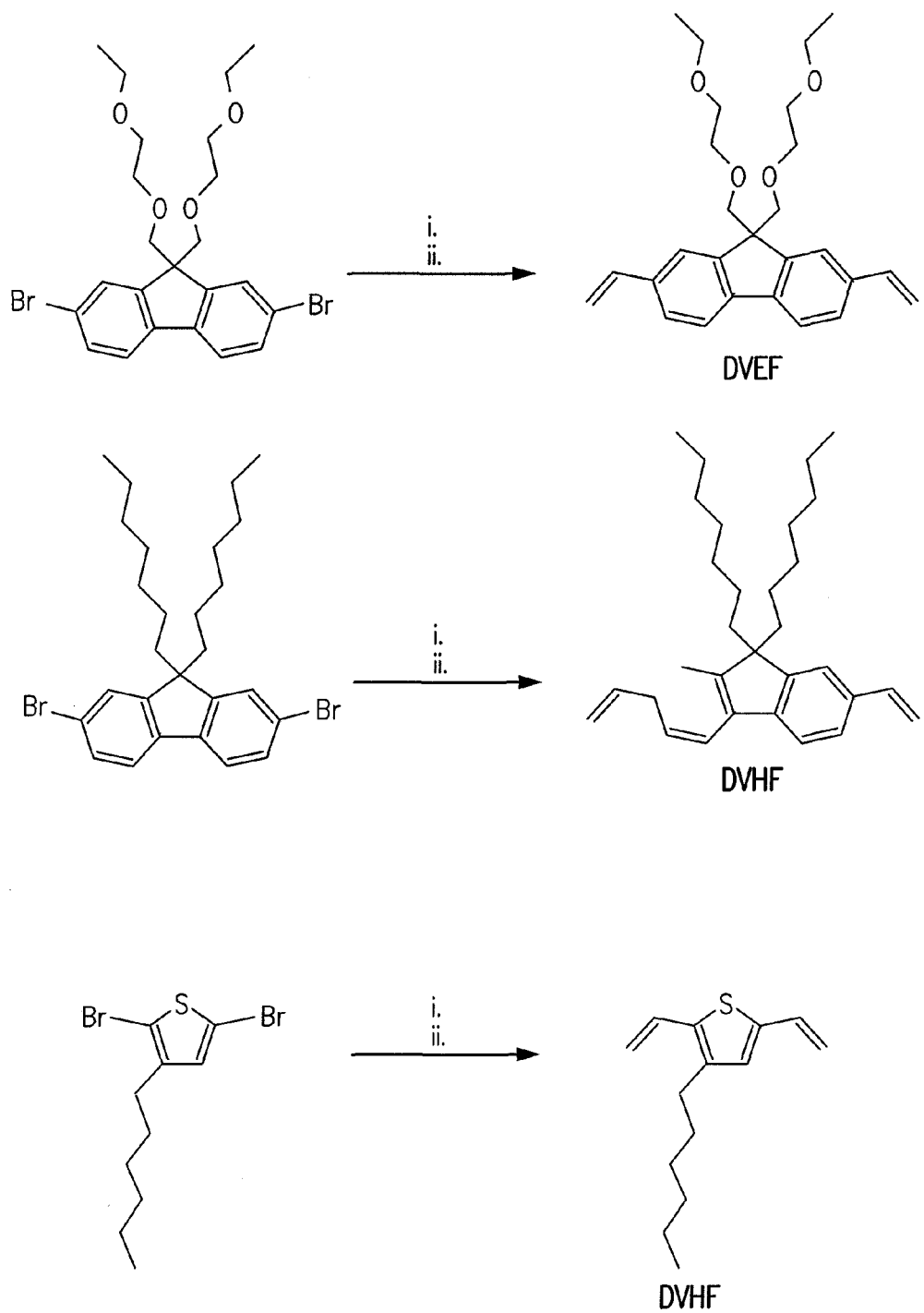
FIG. 1 shows the synthesis of Fluorescent Divinyl Cross-Linker Monomers, 9,9-Bis(2-(2-methoxyethoxy)ethyl)ethyl)-2,7-divinylfluorene (DVEF), 9,9-Dihexyl-2,7-divinylfluorene (DVEF), and 3-Hexyl-2,5-divinylthiophene (DVHT).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular components unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "subject" refers to a living organism as a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In certain aspects, this term can be synonymous with the language "preventative treatment."

As used herein, the term "alleviate" or "alleviating" refers to lightening or lessening the severity of a symptom, condition, or disorder. For example, a treatment that reduces the severity of pain in a subject can be said to alleviate pain. It is understood that, in certain circumstances, a treatment can alleviate a symptom or condition without treating the underlying disorder. In certain aspects, this term can be synonymous with the language "palliative treatment."

As used herein, the term "diagnosed with" a condition refers to having been subjected to a physical examination by a person of skill, for example, a medical doctor (e.g., physician or veterinarian), and found to have the condition. It is also specifically contemplated that a subject (e.g., a mammal, a human) can be identified with such condition.

As used herein, the term "diagnosed with a need for" a treatment refers to having been subjected to a physical examination by a person of skill, for example, a physician, and found to have a condition that can be diagnosed or treated by the treatment. It is also specifically contemplated that a subject (e.g., a mammal, a human) can be identified with a need for such treatment.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In one aspect, administration of a tablet refers to oral administration.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "imaging moiety" refers to any chemical groups or sunstance useful for imaging applications, as known to those of skill in the art. Examples of imaging agents include radioconjugate, cytotoxin, cytokine, Gadolinium-DTPA or a quantum dot, iron oxide, manganese oxide. In one aspect, an imaging agent can be provided in nanoparticular form or in microparticular form. In a further aspect, an imaging agent comprises Gadolinium-DTPA and iron oxide nanoparticles (magnetite), as specific MRI contrast agents. In a yet further aspect, an imaging agent comprises at least one near infrared dye, for example near infrared dyes based on a porphyrin and/or a phthalocyanine. See Ghoroghchian et al., Near-infrared-emissive polymersomes: Self-assembled soft matter for in vivo optical imaging, *PNAS,* 2005, vol. 102, no. 8, 2922-2927.

As used herein, the term "chelating moiety" refers to a bi- or multidentate ligand. Often, chelating moieties form multiple bonds with a single metal ion, thereby forming soluble, complex molecules with certain metal ions, inactivating the ions so that they cannot normally react with other elements or ions to produce precipitates or scale. In one aspect, the chelating moiety forms a chelate complex with the substrate metal.

As used herein, the term "organic quantum dot" refers to a generally carbon based compound having a generally particle-like overall structure and comprising a generally central functional moiety. In one aspect, an organic quantum dot is prepared via formation of a star polymer having a core with a site-isolated chromophore, for example, a fluorophore.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "prepolymer" refers to a polymer of relatively low molecular weight, usually intermediate between that of the monomer and the final polymer or resin, which may be mixed with compounding additives, and which is capable of being hardened by further polymerization during or after a forming process.

As used herein, the term "star polymer" refers to a branched polymer molecule in which a single branch point gives rise to multiple linear chains or arms. The single branch point can be a single chemical moiety or can be a highly crosslinked section of polymer. In one aspect, a star polymer can be generally spherical in shape. In a further aspect, a star polymer can be particle shaped. If the arms are identical the star polymer molecule is said to be regular. If adjacent arms are composed of different repeating subunits, the star polymer molecule is said to be variegated.

As used herein, the term "molecular weight" (MW) refers to the mass of one molecule of that substance, relative to the unified atomic mass unit u (equal to $1/12$ the mass of one atom of carbon-12).

As used herein, the term "number average molecular weight" ($M_n$) refers to the common, mean, average of the molecular weights of the individual polymers. $M_n$, can be determined by measuring the molecular weight of n polymer molecules, summing the weights, and dividing by n. $M_n$, is calculated by:

$$\overline{M}_n = \frac{\sum_i N_i M_i}{\sum_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_w$) refers to an alternative measure of the molecular weight of a polymer. $M_w$ is calculated by:

$$\overline{M}_w = \frac{\sum_i N_i M_i^2}{\sum_i N_i M_i},$$

wherein $N_i$ is the number of molecules of molecular weight $M_i$. Intuitively, if the weight average molecular weight is w, and a random monomer is selected, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" (PDI) refer to the ratio of the weight average to the number average ($M_w/M_n$).

As used herein, the terms "initiator" and "radical initiator" refer to substances that can produce radical species under mild conditions and promote radical polymerization reactions. These substances generally possess bonds that have small bond dissociation energies. Examples include halogen molecules, azo compounds, and organic peroxides. Chlorine, for example, gives two chlorine radicals (Cl•) by irradiation with ultraviolet light. Azo compounds (R—N=N—R') can be the precursor of two carbon-centered radicals (R• and R'•) and nitrogen gas upon heating and/or by irradiation. For example, AIBN and ABCN yield isobutyronitrile and cyclohexanecarbonitrile radicals, respectively. Organic peroxides each have a peroxide bond (—O—O—), which is readily cleaved to give two oxygen-centered radicals. For example, di-t(tertiary)-butylperoxide (tBuOOtBu) gives two t-butanoyl radicals (tBuO•) and the radicals become methyl radicals ($CH_3$•) with the loss of acetone. Benzoyl peroxide ((PhCOO)$_2$) generates benzoyloxyl radicals (PhCOO•), each of which loses carbon dioxide to be converted into a phenyl radical (Ph•).

As used herein, the term "polymerizable group" refers to a group (i.e., a chemical functionality) capable of undergoing a polymerization reaction at a polymerization temperature and/or in response to a polymerization initiator to form a polymer or an oligomer. In one aspect, the polymerization reaction is a radical polymerization (e.g., a vinyl polymerization). It is understood that catalysts can be employed in connection with the polymerization reaction. It is contemplated that, in various aspects, polymerizable groups can be used in step-growth or chain growth reactions. Exemplary polymerizable groups include residues of vinyl, styryl, acryloyl, methacryloyl, aryl, and heteroaryl compounds.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)A' or —C(O)$OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)_a$— or -$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A'C(O)A², where A¹ and A² can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —N₃.

The term "nitro" as used herein is represented by the formula —NO₂.

The term "nitrile" as used herein is represented by the formula —CN.

The term "silyl" as used herein is represented by the formula —SiA¹A²A³, where A¹, A², and A³ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A¹, —S(O)₂A¹, —OS(O)₂A', or —OS(O)₂OA¹, where A¹ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)₂A', where A¹ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A¹S(O)₂A², where A¹ and A² can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A¹S(O)A², where A¹ and A² can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

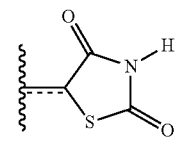

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8 tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. WELL-DEFINED THREE-DIMENSIONAL STRUCTURES

As described in Adkins et al., "Synthesis of Star Polymer Architectures with Site-Isolated Chromophore Cores," MACROMOLECULES, 2008, 41, 3472-3480, star polymers that contain a high degree of chromophores as core functionalities can be prepared and used to investigate site-isolation effects. These architectures represent a class of organic nanostructures that can be further explored toward a higher degree of specificity to integrate functional groups and bioactive organic and inorganic entities.

For the synthesis of star polymer architectures featuring isolated chromophores, the "arm-first" technique was employed, which has demonstrated a high versatility toward a broad range of core monomers and linear macroinitiators. In this approach, entities such as fluorene and thiophene were introduced as cross-linkers to form fluorescent cores in star polymer architectures. The implementation of fluorene and thiophene units as core entities required the modification to divinyl derivatives, which will react with the linear polymer macroinitiators with living dormant chain ends. The cross-linked cores have the luminescence of the monomers rather than of linear poly(thiophenes) and poly(fluorenes), because of the resulting connectivity of the individual cross-linking entities over alkyl chains. Furthermore, the selected monomers were substituted with hexyl (4) and ethylene oxide (EO) units (3) to foster the hydrophobic and hydrophilic character of the star polymers, respectively. The EO derivative was synthesized from 2,7-dibromofluorene and 1-bromo-2-(2-methoxyethoxy)ethane to yield the EO-substituted dibromofluorene monomer for further modification. The conversion of the dibromo units to the reactive divinyl cross-linking derivative was maintained via a Heck reaction previously reported for the synthesis of novel oquinodimethane precursors. Here, the vinyl functionality is achieved in a one-step procedure that encloses an intermediate of a trimethylsilyl-protected vinyl derivative to form the desired divinyl product in good yields after deprotection with TBAF. In this fashion, the dibromo derivatives were converted into their corresponding divinyl (3, 4, and 5) compounds to be investigated as cross-linking units in star polymer formation (FIG. 1).

Figure 2:
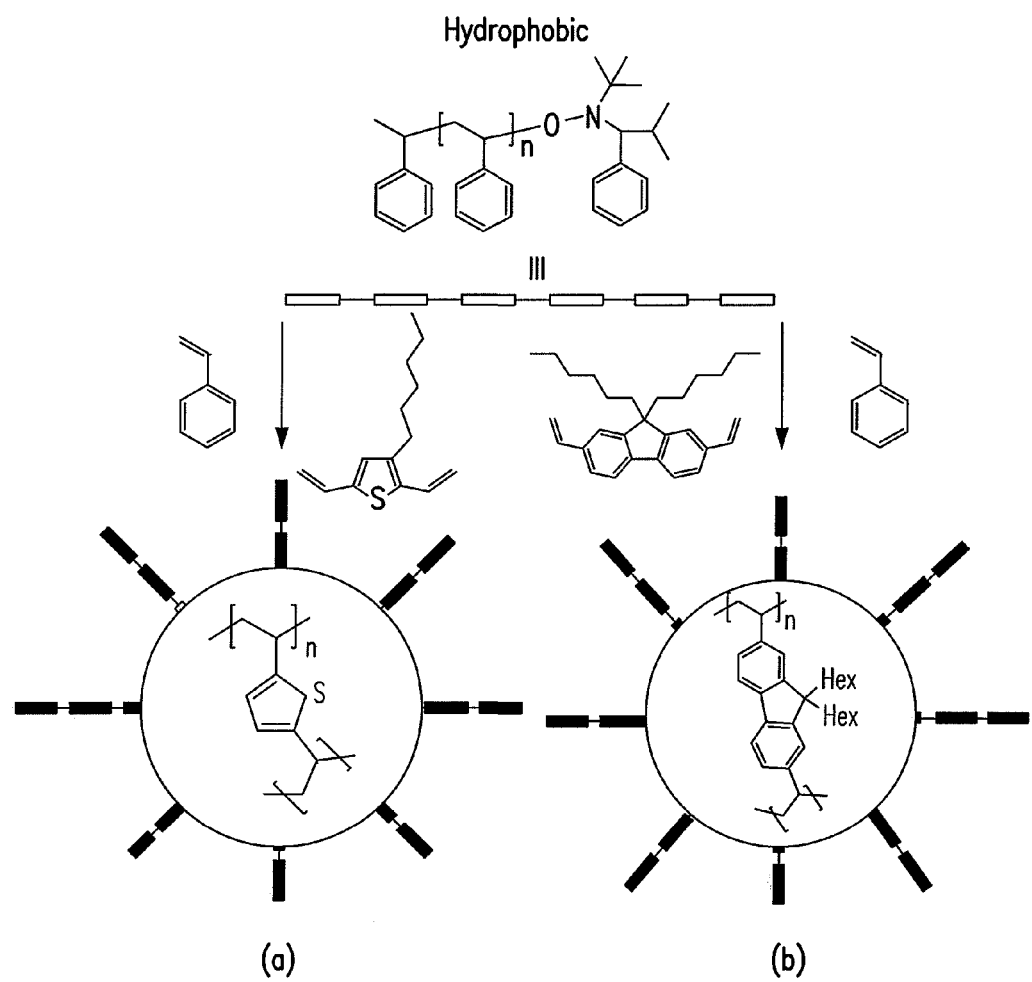
FIG. 2 shows the synthesis of Star Polymers (DVHT PS) (a) and (DVHF PS) (b) Utilizing Divinylhexylthiophene Derivative (DVHT), 5, and Divinylhexylfluorene Derivative (DVHF), 4, as Cross-Linking Units and r-Alkoxyamine-Terminated Macroinitiator (PS).
Figure 3A:
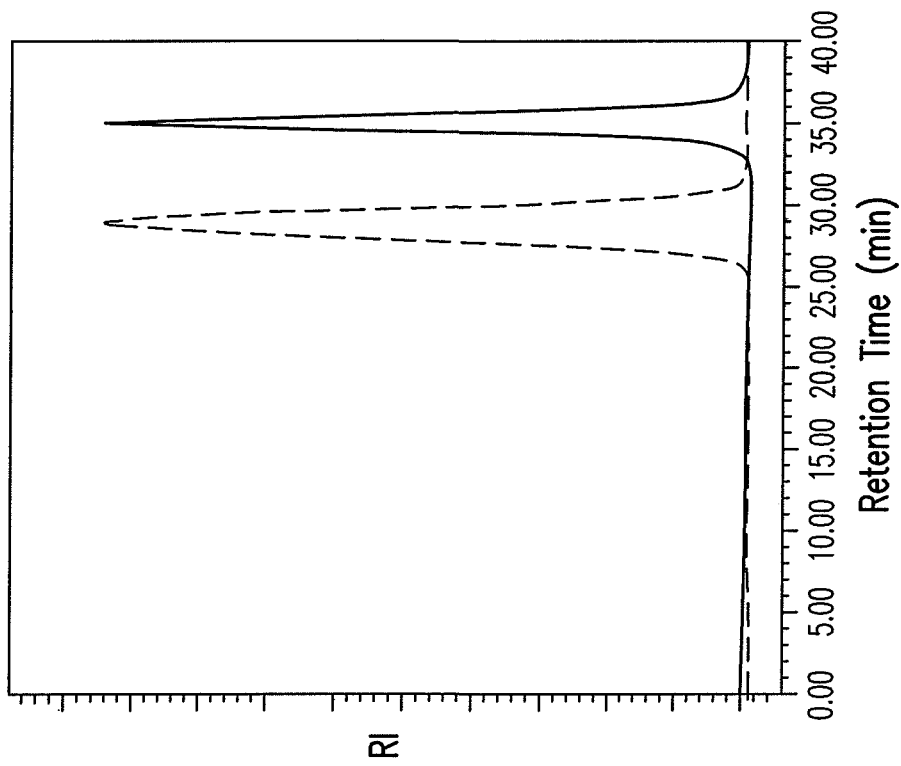
FIG. 3 shows (A) Comparison of gel permeation chromatography (GPC) traces for (a) the R-alkoxyamine-terminated polystyrene macroinitiator, PS, 11 (Mw)) 9.4 kg/mol, PDI (Mw/Mn)) 1.13) and (b) DVHF PS star polymer from [PS]/[DVHF]/[styrene], [PS]) R-alkoxy-terminated polystyrene, [DVHF] divinylhexylfluorene derivative, 4, and styrene as comonomer (Mw) 190 kg/mol, PDI (Mw/Mn)) 1.28) after precipitation. (B) Comparison of GPC traces of (a) R-alkoxyamine-terminated polystyrene macroinitiator PS, 11, and (b) (DVHF PS) star polymer from [PS]/[DVHF]/[styrene], [PS]) R-alkoxy-terminated polystyrene, [DVHF] divinylhexylfluorene derivative, 4, and styrene as comonomer (Mw) 201 kg/mol, PDI (Mw/Mn)) 1.21) after fractional precipitation in acetone/ether.
Figure 3B:
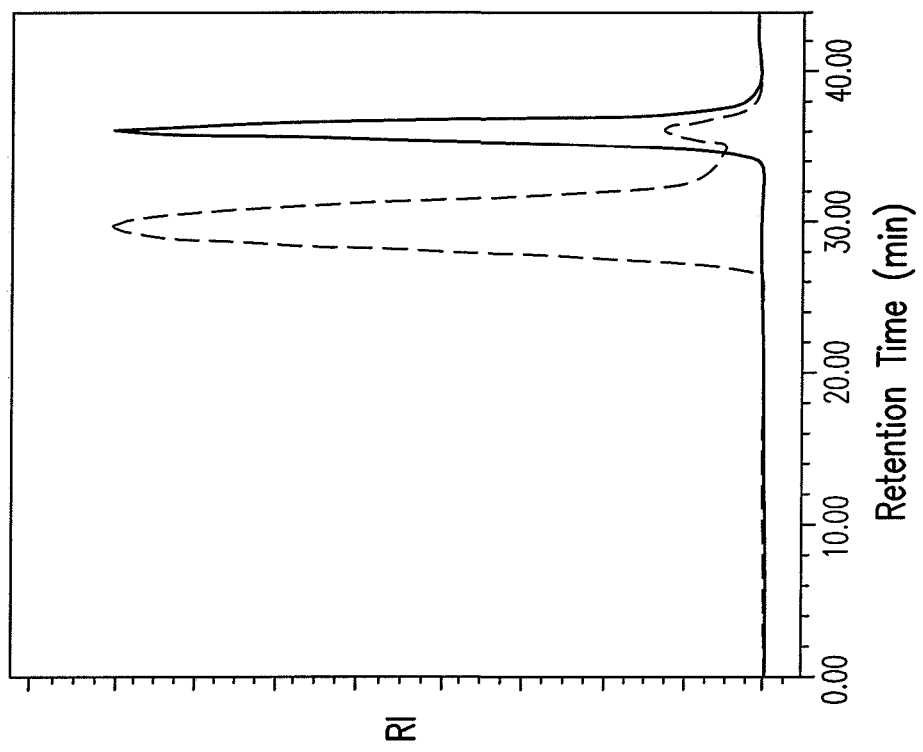

Since the amount of cross-linking agent can affect star formation, several trials were employed to determine the appropriate feed ratio of cross-linking agent to macroinitiator with the diverse cross-linkers prepared. In the preparation of star polymer architectures DVHF PS cross-linked star polymers (FIG. 2) were employed. Initial trials involved a feed ratio of [PS]/[DVHF]/[styrene]) 1/3.5/10 (9) (Table 1); however, gel formation was observed. When smaller amounts of cross-linker, such as a feed ratio of [PS]/[DVHF]/[styrene]) 1/3.2/10, were introduced, star polymer formation (10) was observed. However, these stars possessed rather large polydispersities (1.5-1.9). A feed ratio of [PS]/[DVHF]/[styrene]) 1/3.2/8 gave well-defined DVHF PS star polymers in relatively high percent yield (84%) (11) (FIG. 1).

TABLE 1

REPRESENTATIVE EXPERIMENTS FOR DVHF PS POLYMER STARS

| entry | $M_{w, RI}$ (kg/mol)[a] | reactant ratio (PS/DVHF/styrene)[b] | $M_{w, RI}$ (kg/mol)[c] | PDI[d] |
|---|---|---|---|---|
| 9 | 1.2 | 1/3.5/10 | | |
| 10 | 1.2 | 1/3.2/10 | 115 | 1.61 |

TABLE 1-continued

REPRESENTATIVE EXPERIMENTS FOR DVHF PS POLYMER STARS

| entry | $M_{w, RI}$ (kg/mol)[a] | reactant ratio (PS/DVHF/styrene)[b] | $M_{w, RI}$ (kg/mol)[c] | PDI[d] |
|---|---|---|---|---|
| 11 | 9 | 1/3.2/8 | 190 (254)[e] | 1.28 |

[a]R-Alkoxy-terminated polystyrene PS, weight-average molecular weight (Mw) after purification.
[b]Star polymer (DVHF PS) from [PS]/[DVHF]/[styrene], [PS]) R-alkoxy-terminated polystyrene, [DVHF] divinylhexyl fluorene derivative, 4, and styrene as comonomer.
[c]Weight-average molecular weight (Mw) after precipitation; gel permeation chromatography (GPC) data relative to PS standards.
[d]Polydispersity (PDI) Mw/Mn), measured by GPC with tetrahydrofuran as eluent and integrated RI detector; calibration with linear PS as standard.
[e]Weight-average molecular weight, measured by static light scattering (SLS).

Initially, the synthesis of thiophene star polymers (DVHT PS, FIG. 2) was employed with equivalent conditions that had been successful for the formation of well-defined DVHF PS stars (Table 1) since comparable conditions applied in relation to type, amount of solvent, and temperature. However, a significantly larger amount of cross-linker was necessary to form DVHT PS star polymers. Preliminary experiments involved the use of relatively small amounts of cross-linking agent. Feed ratios of [PS]/[DVHT]/[styrene]) 1/3.2/8 lead to oligomer formation (12(a)), corresponding to region a of FIG. 2. Upon introduction of considerably larger amounts of cross-linker, with a feed ratio of [PS]/[DVHT]/[styrene]) 1/15/8, star polymer (17(d)) formation was observed (Table 2, region d in FIG. 2).

TABLE 2

REPRESENTATIVE EXPERIMENTS FOR DVHT PS POLYMER STARS

| entry | Mw, RI (kg/mol)[a] | reactant ratio[b] (PS/DVHT) | Mw, RI (kg/mol)" | PDI[d] |
|---|---|---|---|---|
| 12(a) | 9.3 | 1/3.2 | 21 | 1.34 |
| 13(a) | 9.2 | 1/3.6 | 22 | 1.09 |
| 14(a) | 9.2 | 1/3.9 | 22 | 1.07 |
| 15(b) | 7.2 | 1/6.5 | 23 | 1.28 |
| 16(d) | 7.2 | 1/11.6 | 49 (98)[e] | 1.58 |
| 17(d) | 7.2 | 1/14.9 | 70 (140)[e] | 1.83 |

Figure 4:
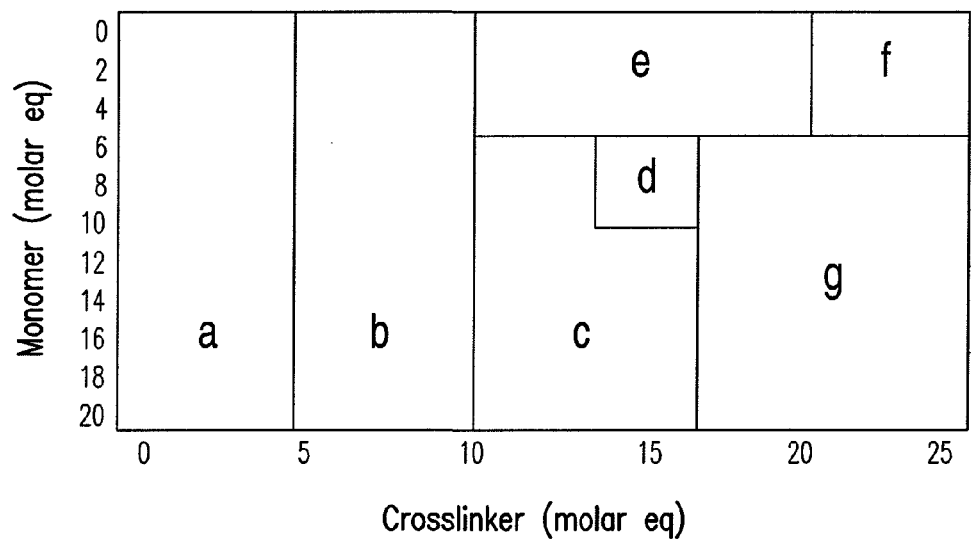
FIG. 4 shows DVHT PS star polymer formation. Regions a and b: primarily oligomerized linear polymer chains; region c: high molecular weight products, high polydispersity stars; region d: high molecular weight, low polydispersity stars; region e: low molecular weight, high polydispersity stars; region f: high molecular weight, high polydispersity stars; region g: gel formation.

Only five initial trials were necessary to determine the region and starting point for star polymer formation. See FIG. 4. Representative experiments of these trials are summarized in Table 2. Once appropriate parameters for star polymer formation were verified, it was necessary to further adjust the parameters to define the entire region of well-defined star polymer formation. In order to evaluate the time point for the optimum star polymer yield that results in low polydispersity stars with high conversion and high molecular weight, samples were taken at time points from 8 to 72 h. In general, the conversion below 16 h was too low and above 24 h gave high molecular weight stars with high polydispersities. In these experiments, the most well-defined star polymers from polystyrene macro-initiators were formed at 16 h.

In order to synthesize water-soluble star polymers, linear polyacrylates (PAA) were synthesized via the RAFT polymerization procedures. The RAFT approach was selected because of its facile application to a wide range of functional groups, such as OH, $NH_2$, and COOH. In the synthesis of star polymers derived from RAFT polymerization techniques, the use of PAA macroinitiators from highly efficient dithioester chain transfer agents (CTA), such as 4-cyanopentanoic acid dithiobenzoate and also 2,2'-dimethylpropionate dithiobenzoate was employed. It was observed that the quality of the linear polyacrylates did not significantly vary by the use of the two initiators mentioned above, but we chose to continue the synthesis of the polyacrylates with the reported 4-cyanopentanoic dithiobenzoate that gave well-defined polyacrylate macroinitiators with low polydispersities of 1.12.

Several aspects of the RAFT star polymer synthesis differed from the NMP method. Initial experiments followed the same procedure as the NMP star synthesis, which included the reaction of macroinitiator with cross-linker and comonomer. However, it was determined that comonomer was not required in RAFT star polymer synthesis. Moreover, RAFT star formation required a radical starter, such as AIBN, to reinitiate polymerization of the macroinitiator. The temperature proved also to be a factor in the star polymer formation. Although some RAFT polymerization techniques are conducted at 70° C., star polymer formation did not typically take place at such a low temperature and was elevated to 85° C. to initiate star polymer synthesis. The RAFT star polymer synthesis was begun with cross-linker amounts comparable to DVHF PS stars. With a feed ratio of [PAA]/[DVEF]/[AIBN] =1/3.2/0.20, star polymer formation was not observed, and larger amounts of cross-linker were introduced to achieve high quality star polymers.

Figure 5:
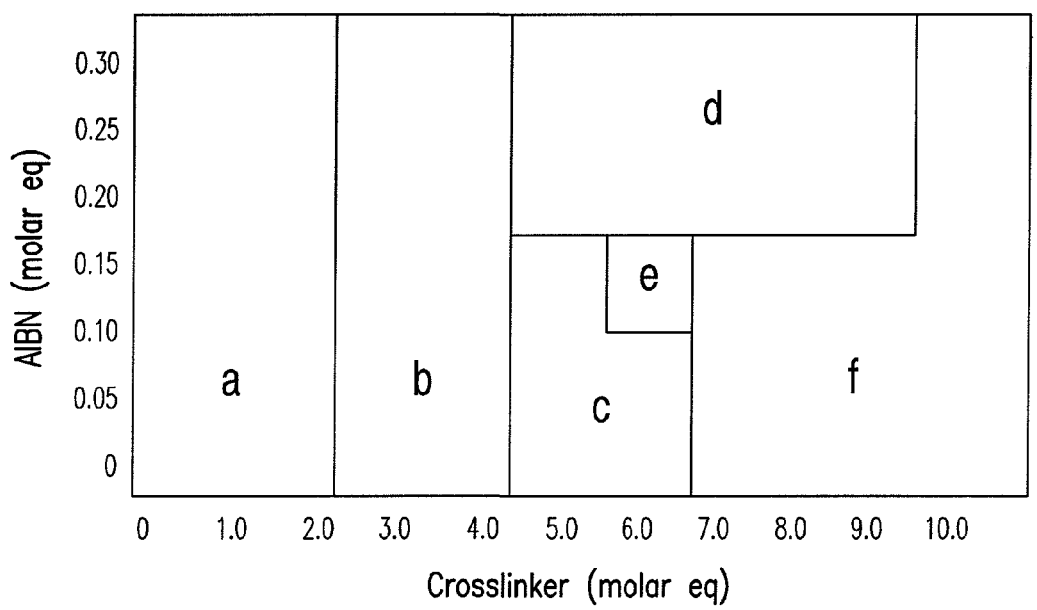
FIG. 5 shows DVEF PAA star polymer formation. Regions a and b: oligomerized linear polymer chains; region c: oligomerized stars, low molecular weight products, low polydispersity; region d: low molecular weight, high polydispersity stars; region e: high molecular weight, low polydisperisty stars; region f: high molecular weight, high polydispersity stars.
Figure 6:
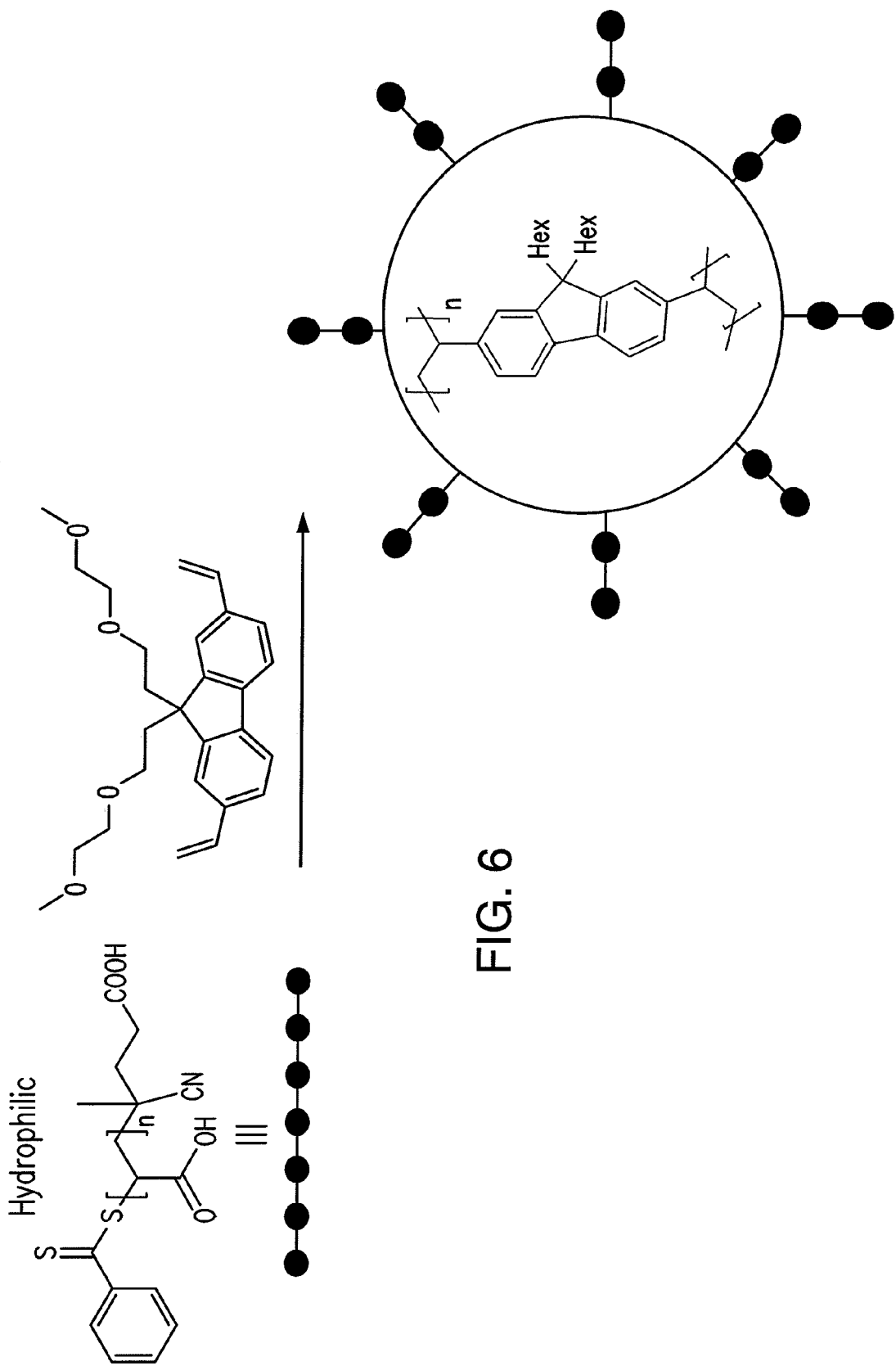
FIG. 6 shows synthesis of ethylene oxide (EO) fluorene Star Polymers (DVEF PAA) Utilizing Divinylethoxyfluorene Derivative (DVEF), 3, as Cross-Linking Units and Dithioester End-Capped Polyacrylate Macroinitiator (PAA).

With the addition of nearly twice as much cross-linker as required in DVHF PS star synthesis, well-defined nanostructures displaying a low polydispersity (FIG. 5) were formed. The optimum feed ratio for successful star formation displaying a low polydispersity and high molecular weight was determined to be [PAA]/[DVEF]/[AIBN]) 1/6.0/0.10 (23(e)) after a series of trials. As shown for the polystyrene star synthesis (FIG. 6), the optimum star polymer yield was evaluated by verifying the conversion at different time points during synthesis. Samples were taken during a time frame of 8-96 h. It was found that less than 24 h led to oligomers, while at duration times above 24 h star polymer formation was observed. At 48 h conditions for low polydispersity and high molecular weight star polymer were found to be at optimum values together with high conversion rates. Longer reaction times decreased the quality of the stars, and high polydispersity star polymers were formed. Representative experiments are summarized in Table 3 and give the feed ratios for the characteristic regions identifying ideal conditions for star polymer synthesis which are shown in FIG. 5.

In order to complete the characterization of the synthesized star polymer architectures, we employed dynamic light scattering techniques to determine the diameter and employed static light scattering methods for the absolute molecular weight measurements. DVHF PS stars displayed an average size of 11 nm, owing to the smaller amount of cross-linker incorporated, in contrast to DVEF PAA stars that exhibited an average size of 20 nm and DVHT PS stars with an average size of 90 nm due to the even higher amount of cross-linking unit necessary to form well-defined star polymers. In respect to molecular weight measurements, DVHF PS star polymers maintained an absolute molecular weight of 250 kDa, while DVEF PAA star polymers had an average absolute molecular weight of 185 kDa, corresponding to 30-40 arms per nanostructure while DVHT stars displayed an average absolute molecular weight of 330 kDa.

Figure 7:
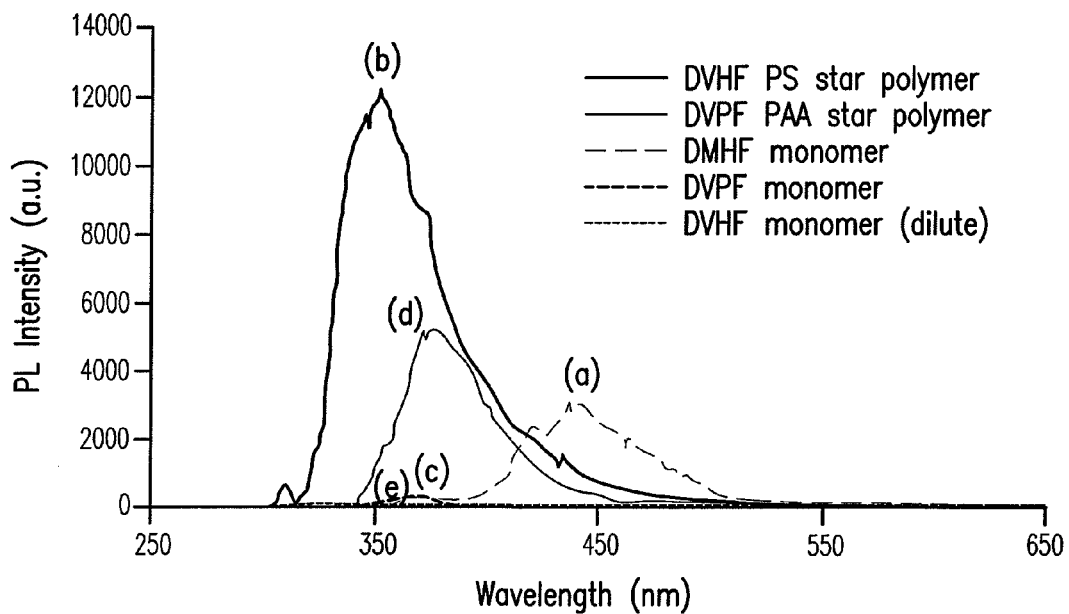
FIG. 7 shows photoluminescence (PL) spectra of (a) DVHF monomer, 4, in solution ($2 \times 10^{-3}$ mM in cyclohexane), (b) DVHF PS star polymer 11 in solution ($2 \times 10^{-3}$ mM in cyclohexane), (c) DVEF, 3, monomer in solution ($2 \times 10^{-3}$ mM in cyclohexane), (d) DVEF PAA star polymer 23 in solution ($2 \times 10^{-3}$ mM in methanol), and (e) DVHF monomer, 4, in dilute solution ($1 \times 10^{-3}$ mM).

The resulting conformation and environment of the chromophores as core entities in the star polymeric architectures were probed by UV-vis absorption and photoluminescence measurements in solution. The photoluminescence properties (PL) of the star polymers containing fluorene-derived core entities were investigated, which were recorded by excitation at the absorption maximum. FIG. 7 shows that the star polymer from linear R-alkoxyamine-terminated polystyrene (DVHF PS, 11) with incorporated DVHF (4) displayed an absorption and emission wavelength of 313 and 353 nm, respectively. The emission maximum of the DVHF monomer 4 displayed two maxima depending on the concentration in solution at 423 and 434 nm and at 367 nm for the lowest concentration. Analogous results were obtained for the DVEF PAA polymeric stars with an absorption wavelength of 340 nm and emission wavelength of 376 nm, with the DVEF monomer emitting at 367 nm. It was also observed an almost doubled PL intensity of the emission spectra of the star polymer architectures in contrast to the monomer as a result of the cross-linking event during star polymer formation. Without wishing to be bound by theory, it was concluded that cross-linked core structures prevent $\pi$-stacking of the chromophores maintained by the sterical hindrance of the hexyl and EO-functionalized divinyl derivatives as well as a reduction of the extinction among molecules and increase in $\pi$-$\pi$* transition energies in contrast to the monomers in solution. Additionally, the cross-linking event enhances the structural disorder of monomers in close proximity to each other that increases the binding energy of the excitons and leads to increase in photoluminescence. It was further observed that strongly diluted divinyl monomers 3 and 4 emitted at nearly the same wavelength as the star polymers 11 and 23 but with a much lower photoluminescence. Together with this observation, it is indicated that the site-isolated cross-linking units show electronic features of individual chromophores while avoiding fluorescence quenching and a red shift by aggregation effects seen in concentrated monomer solutions such as demonstrated for the DVHF monomer. At the same time, the conformation of the core chromophores displayed a highly localized concentration of connected but disordered chromophores that lead to a much higher PL intensity.

Figure 8:
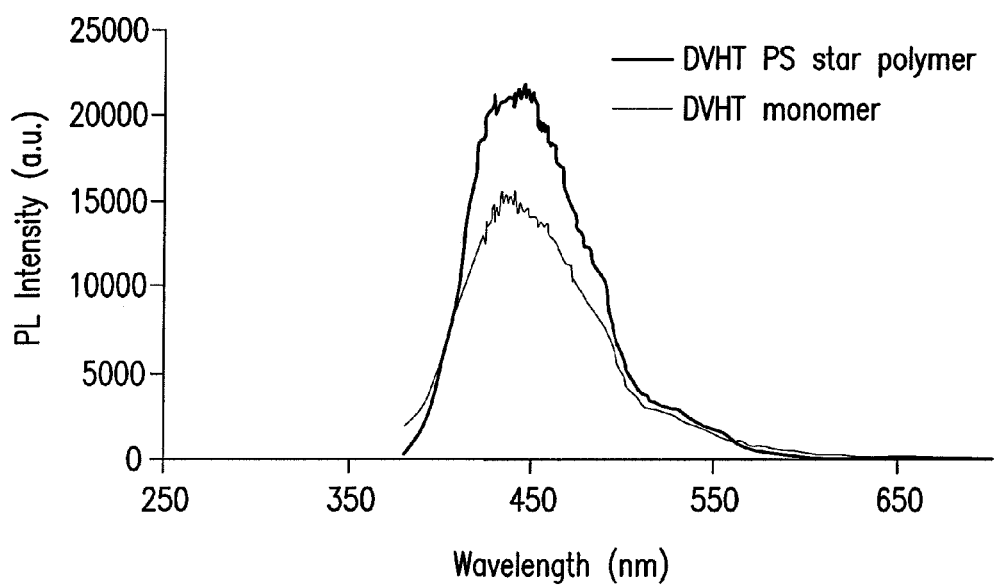
FIG. 8 shows photoluminescence (PL) spectra of DVHT monomer, 5, and star polymer DVHT PS, 23, in solution ($3 \times 10^{-3}$ M in cyclohexane).
Figure 9:
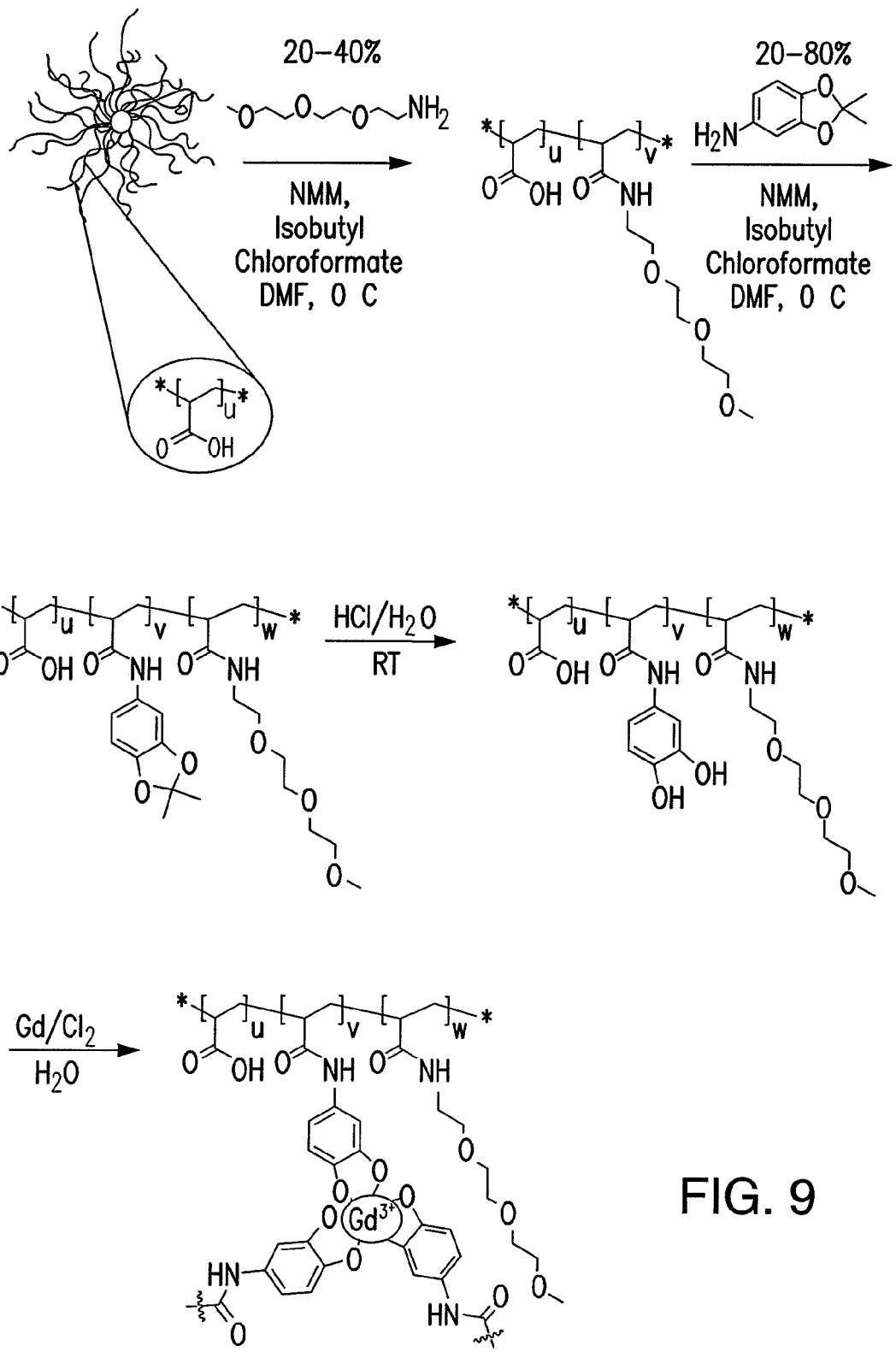
FIG. 9 shows modification of EO fluorene star polymer with catechol unit for $Gd^{3+}$ chelation.
Figure 10:
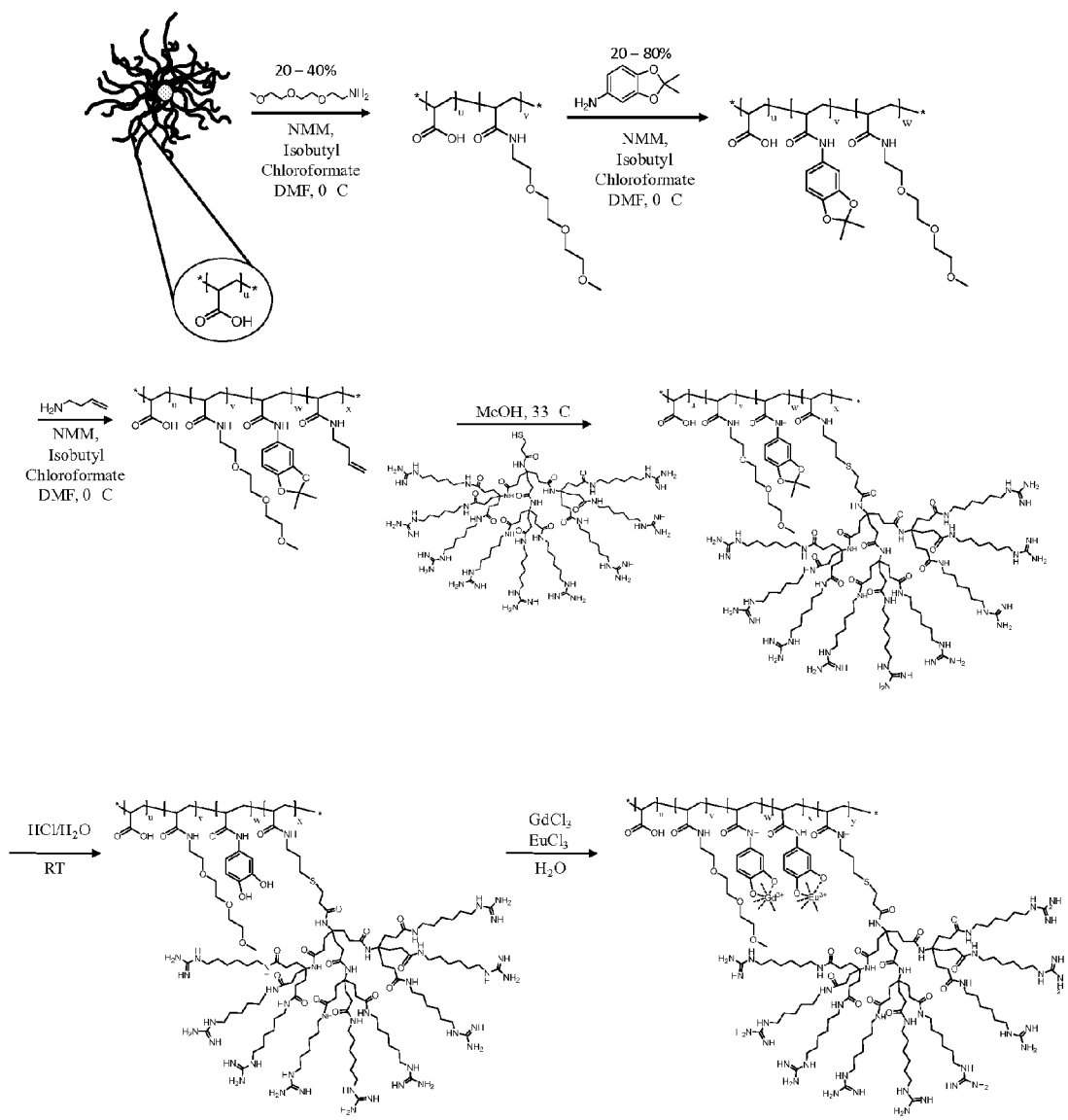
FIG. 10 shows synthesis of bimodal imaging agent with molecular transporter for crossing biological barriers.
Figure 11:
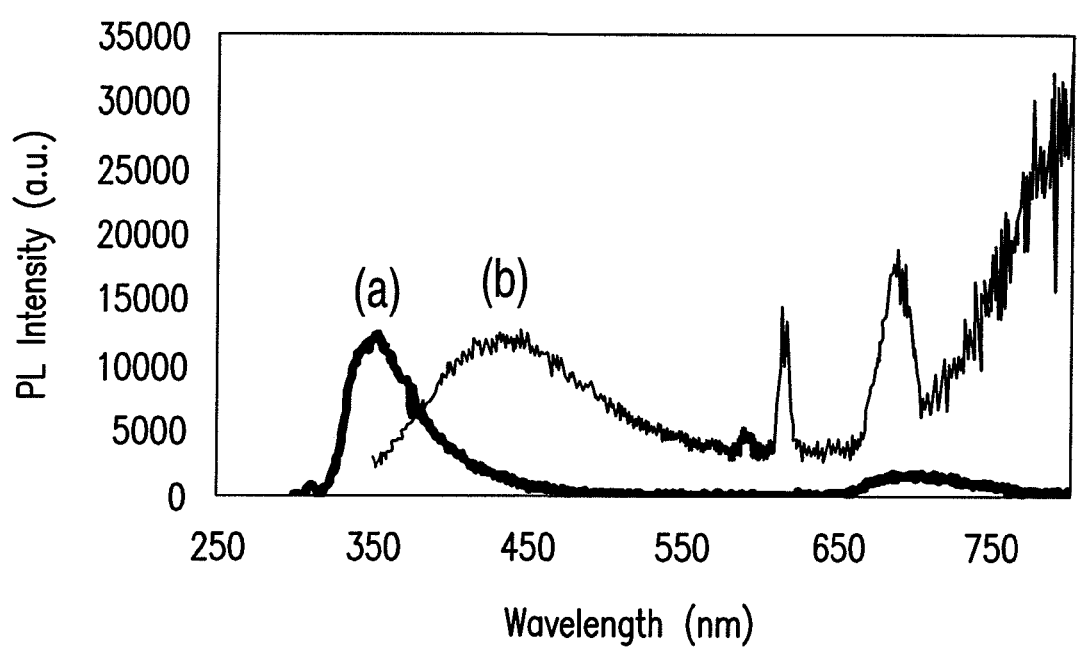
FIG. 11 shows photoluminescence spectra of (a) EO fluorene star polymer and (b) molecular transporter modified star polymer with $Gd^{3+}$ and $Eu^{3+}$.
Figure 12:
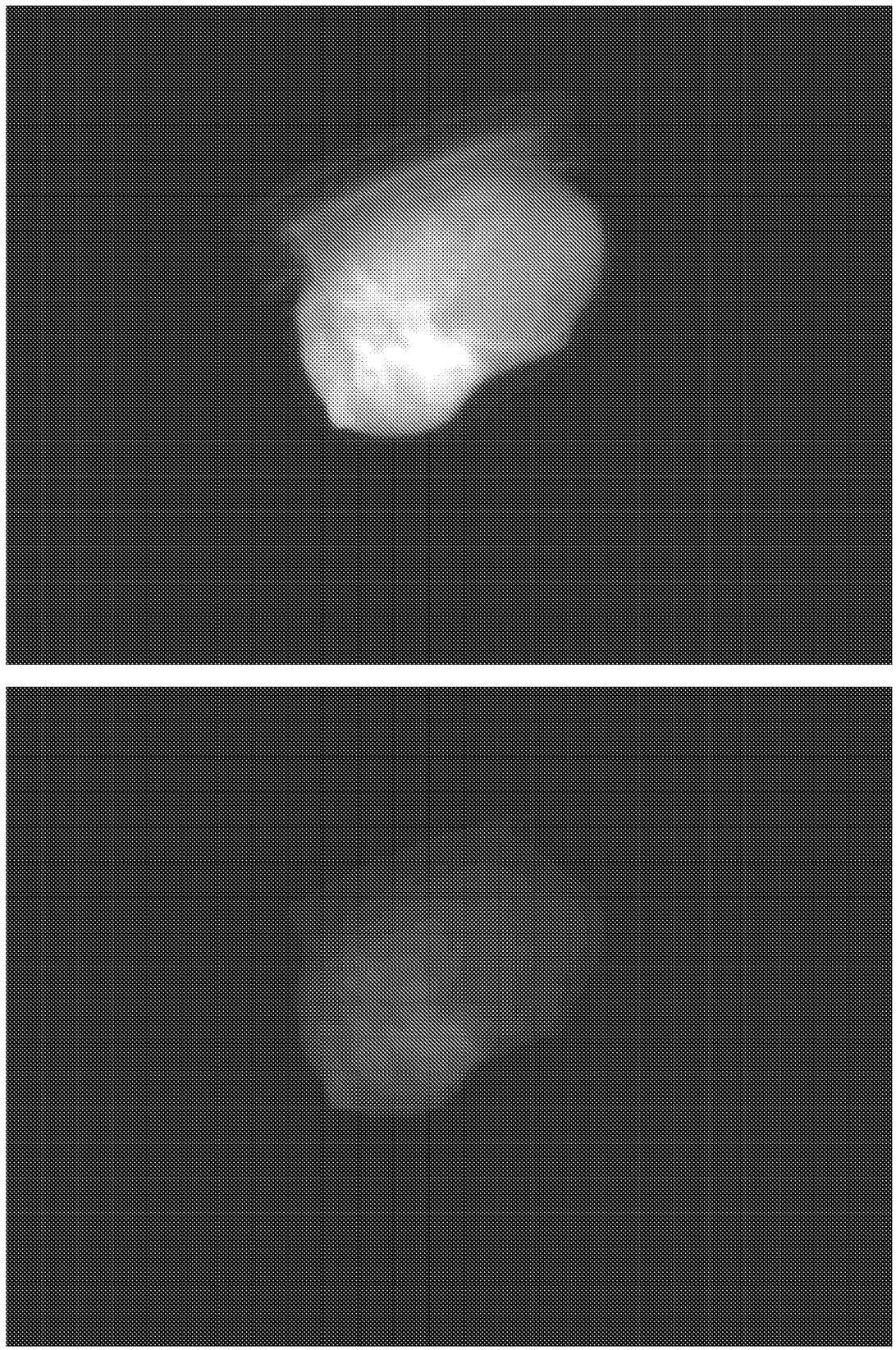
FIG. 12 shows images of exised mouse heart (t=0.5 h after injection) using the inventive compositions and methods (Star polymer with 2000 MW PEG (See Experimental 21), Alexa fluor dye, and otherwise untreated mouse; Maestro Instrument) in black & white image (top, intense white color) as well as color image (bottom, intense red color).
Figure 13:
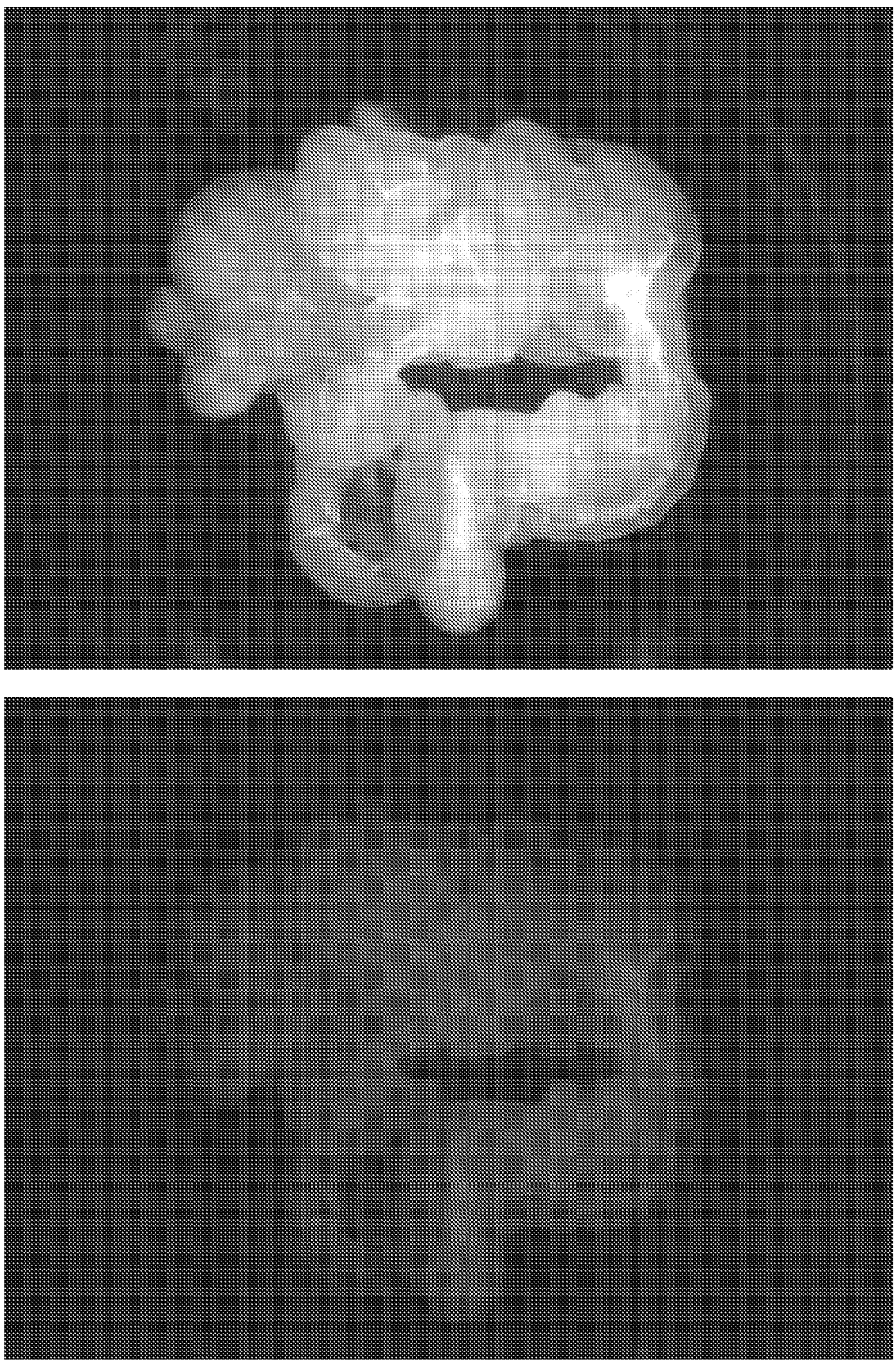
FIG. 13 shows images of exised mouse gastrointestinal system (t=0.5 h after injection) using the inventive compositions and methods (Star polymer with 2000 MW PEG (See Experimental 21), Alexa fluor dye, and otherwise untreated mouse; Maestro Instrument) in black & white image (top, intense white color) as well as color image (bottom, intense red color).
Figure 14:
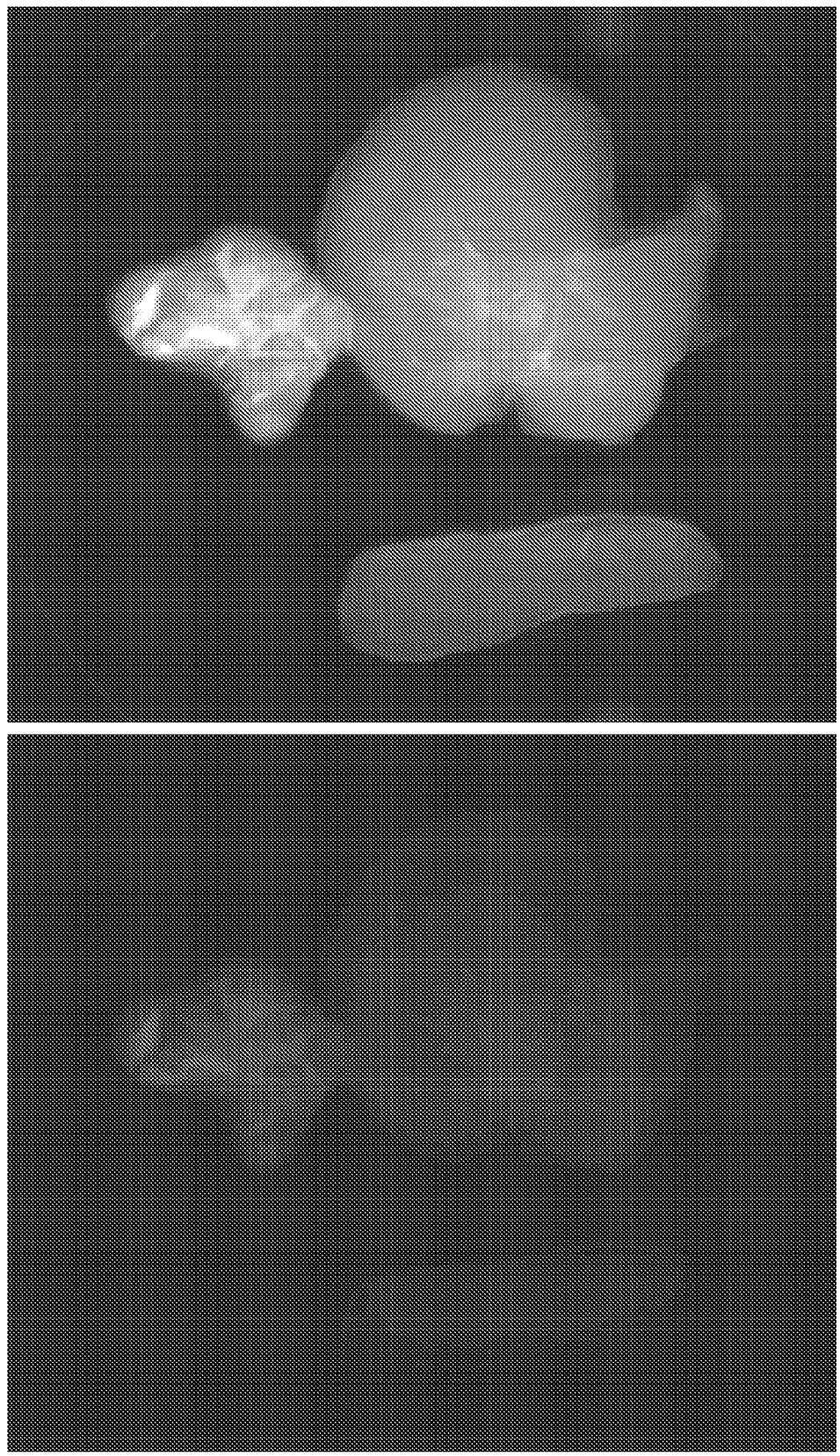
FIG. 14 shows images of exised mouse liver, lungs, and spleen (t=1 h after injection) using the inventive compositions and methods (Star polymer with 2000 MW PEG (See Experimental 21), Alexa fluor dye, and otherwise untreated mouse; Maestro Instrument) in black & white image (top, intense white color) as well as color image (bottom, intense red color).
Figure 15:
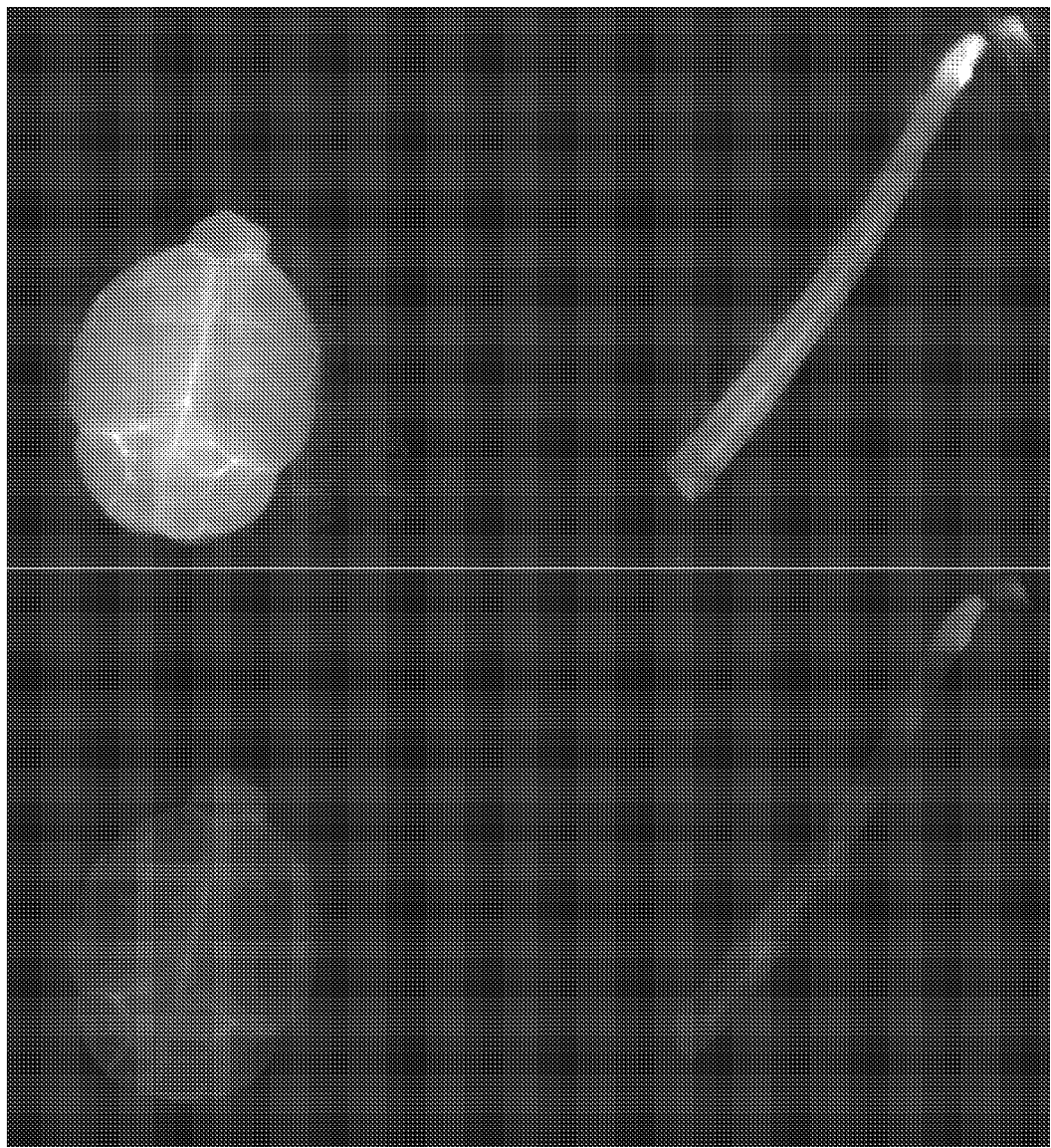
FIG. 15 shows images of exised mouse brain and tail (t=1 h after injection) using the inventive compositions and methods (Star polymer with 2000 MW PEG (See Experimental 21), Alexa fluor dye, and otherwise untreated mouse; Maestro Instrument) in black & white image (top, intense white color) as well as color image (bottom, intense red color).
Figure 16:
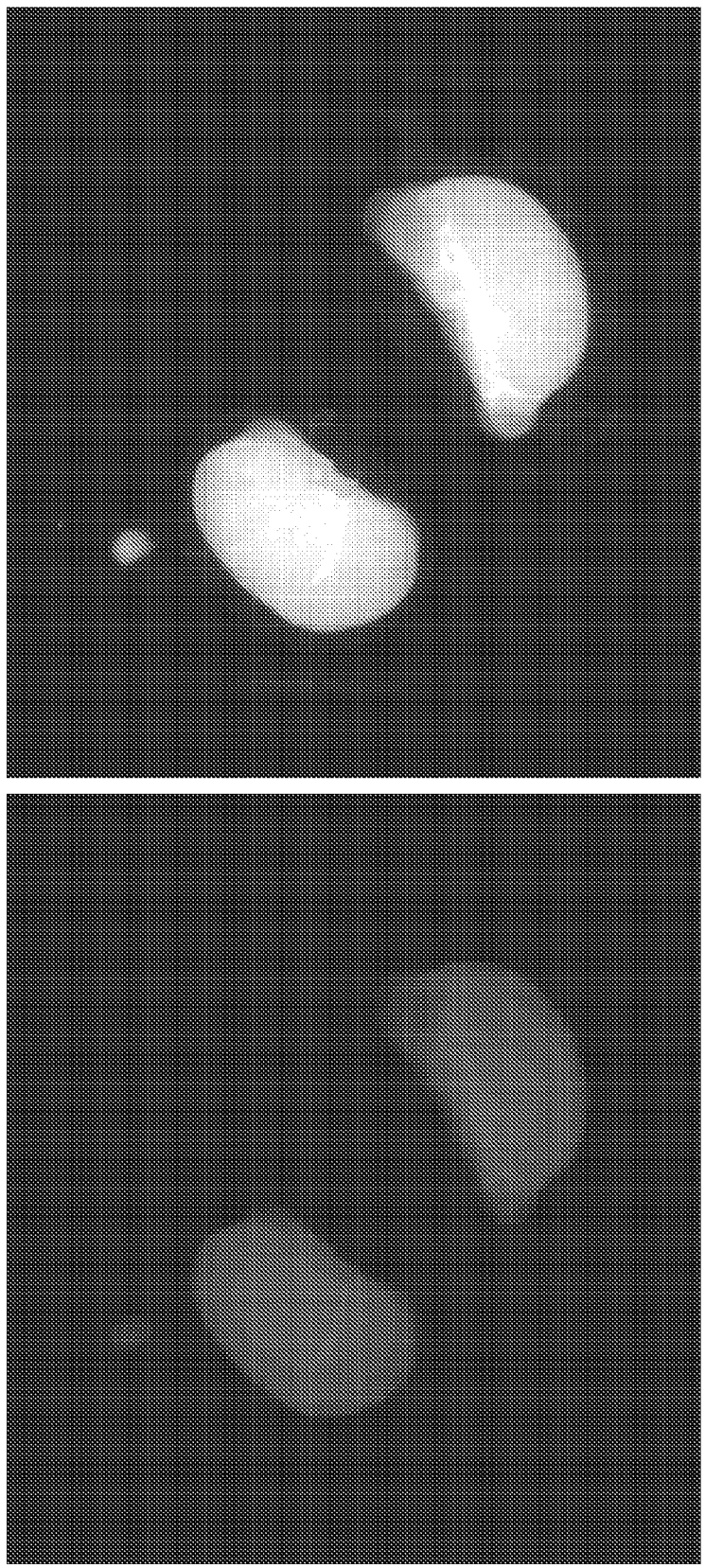
FIG. 16 shows images of exised mouse kidneys (t=0.5 h after injection) using the inventive compositions and methods (Star polymer with 2000 MW PEG (See Experimental 21), Alexa fluor dye, and otherwise untreated mouse; Maestro Instrument) in black & white image (top, intense white color) as well as color image (bottom, intense red color).

The star polymer architectures that are comprised with thiophene cross-linking units displayed similar electro-optical characteristics. The thiophene star polymers from R-alkoxyamine terminated polystyrene displayed absorption and emission wavelengths of 370 and 434 nm, respectively, while thiophene monomer (5) had an emission wavelength of 434 nm (FIG. 8). The PL intensity increased by 10%, also caused by a sterically induced reduction of extinction and increased isotropy through the cross-linking during star polymer synthesis in addition to an increased quantum yield of 3.2%. Also here, the conformation of the chromophores in the star polymer systems suggested connectivity over individual chromophore entities, as the optical properties from photoluminescence spectroscopy indicated. In comparison to the fluorene star polymers, these results demonstrated that conformational changes of the cross-linked monomer are specifically pronounced in monomer units that extend one aromatic system and are more prone to $\pi$-stacking and aggregation in solution.

TABLE 3

REPRESENTATIVE EXPERIMENTS FOR DVEF PAA POLYMER STARS

| entry | $M_{w,RI}$ (kg/mol)[a] | reactant ratio[b] (PAA/DVEF) | $M_{w,RI}$ (kg/mol)[c] | PDI[d] |
|---|---|---|---|---|
| 18(a) | 6.2 | 1/1.8 | 25 | 1.12 |
| 19(b) | 6.2 | 1/2.5 | 30 | 1.23 |
| 20(b) | 7.3 | 1/3.0 | 33 | 1.24 |
| 21(b) | 7.3 | 1/3.5 | 33 | 1.24 |
| 22(e) | 9.0 | 1/5.2 | 36 (70)[d] | 1.29 |
| 23(e) | 7.7 | 1/6.0 | 69 (185)[e] | 1.32 |

[a]Dithioester end-capped polyacrylate macroinitiator (PAA), weight-average molecular weight (Mw) after purification.
[b]Star polymer (DVEF PAA) from [PAA]/[DVEF], [PAA] = dithioester end-capped polyacrylate, [DVEF] divinylethoxy fluorene derivative, 3.
[c]Weight-average molecular weight (Mw) after dialysis; gel permeation chromatography (GPC) data relative to polystyrene standards.
[d]Polydispersity (PDI = Mw/Mn), measured by GPC with tetrahydrofuran as eluent and integrated RI detector; calibration with linear PS as standard.
[e]Weight-average molecular weight, measured by static light scattering (SLS).

The controlled preparation of functionalized soft materials has rapidly become a vital research topic due to their various applications in nanotechnology such as molecular imaging. In particular, magnetic resonance imaging (MRI) is a powerful technique in diagnostic clinical medicine and biomedical research that enables the acquisition of high resolution, three-dimensional images of the distribution of water in vivo. This imaging method relies on the use of pharmacological products, called contrast agents which aid in the detection of structural abnormalities in the body. These contrast agents contain paramagnetic compounds such as $Gd^{3+}$ to shorten the proton relaxation time of nearby water molecules, thereby enhancing the contrast with background tissues. While MRI is a widely used technique, there is a great demand for more efficient MRI contrast agents that allow the incorporation of a large amount of paramagnetic compound to afford a more intense signal than the current compounds. Consequently, it is necessary to create a suitable scaffold from which this can be achieved. It is also desirable to create imaging agents that possess multiple features to allow the analysis of different diagnostic procedures from a single compound. Therefore, it is desirable to create a structure that 1) allows a higher payload of paramagnetic compound than current contrast agents and 2) possesses a mixture of features (e.g. magnetic and fluorescent).

Thus, chemical strategies have also been developed to create water soluble star polymer architectures that are composed with site-isolated chromophore cores from tailored fluorescent monomers and poly (acrylic acid) linear polymer arms modified with gadolinium or europium chelates, dendritic molecular transporters, and/or cRGD as targeting units. Metals, such as gadolinium or europium, can be chelated to catechol units to give high contrast agents. A feature in the design of the agents lies in the small catechol units that are available. Catechol derivative units were successfully attached and, thus, available for the chelation of gadolinium and europium to poly(acrylic acid) arms in the star polymers.

An increase in photoluminescence indicates site-isolation effects in star polymers, while the emanating linear polymers are available for further functionalization of aqueous soluble star polymers. With the presence of both magnetic and fluorescent features, extremely potent imaging agents were produced, yielding high relaxivity values. Further modification allowed the attachment of targeting units such as a dendritic molecular transporter in order to cross biological barriers.

Star polymers with semiconducting cores from tailored fluorescent monomers were modified with gadolinium chelates and studied as magnetic resonance imaging (MRI) agents with hydrodynamic diameters of 10±2 nm. The properties of these materials, which include non-toxicity towards mammalian cells and capability for cell targeting, make them ideal candidates for use within biological systems. An amine terminated dopamine derivative allowed for the covalent conjugation to acrylate based star polymers. The highly hydrated nature of the star polymer on which the $Gd^{3+}$ was located allowed for rapid water exchange therefore, the resulting material displayed large ionic relaxivities (79 $mM^{-1}s^{-1}$) in an applied magnetic field of 0.5 T at 37° C.

In developing fluorescent star polymers, it was necessary to synthesize well-defined linear building blocks. Reversible addition fragmentation chain transfer (RAFT) techniques were utilized to synthesize poly(acrylic acid) macroinitiators with narrow polydispersities and controlled molecular weights. Additionally, aqueous soluble ethylene oxide substituted fluorene crosslinking agents were made. Optimum conditions for aqueous soluble star polymers of ethylene oxide fluorene poly(acrylic acid) (DVEF PAA) were developed.

Upon determining the ideal conditions to synthesize well-defined star polymers, the resulting conformation and environment of the chromophores in the star polymeric architectures were probed by UV-Vis absorption and photoluminescence (PL) measurements. The DVEF PAA star polymers displayed an absorption and emission wavelength of 340 nm and 376 nm, respectively, with the DVEF monomer emitting at 367 nm. An almost doubled PL intensity of the emission spectra of the star polymer architectures was observed, in contrast to the monomer as a result of the cross-linking event during star polymer formation. It was determined that cross-linked core structures prevent π-stacking of the chromophores maintained by the sterical hindrance of the ethylene oxide functionalized divinyl derivative. This observation indicates that the site-isolated cross-linking units show electronic effects of individual chromophores, while avoiding fluorescence quenching effects seen in concentrated monomer solutions.

In designing a novel nanoparticulate contrast agent, it was necessary to synthesize lanthanide complexing units capable of withstanding living free radical polymerization. Consequently, it was selected to graft catechol units onto the water soluble star polymers. The deprotection of said catechol unit was straightforward, followed by chelation of $Gd^{3+}$ and $Eu^{3+}$ for magnetic and fluorescent features, respectively. Extremely large (between 25-80 $mM^{-1}s^{-1}$) relaxivity values were obtained. These polymers were further functionalized by the attachment of dendriditic molecular transporters and peptide units. 3T3 cells were treated with these materials, and cell uptake into the cytosol was noted in a matter of 10 minutes. These cells with modified star polymers exhibited blue, green, and red fluorescence emissions.

TABLE 4

GD(III) IONIC AND MOLECULAR RELAXIVITIES OF
THE MRI CONTRAST AGENTS AT 20 MHz, 20° C.

| Paramagnetic Chelate | Gd ionic $r_1$ ($mM^{-1}s^{-1}$) | no. of $Gd^{3+}$ | molecular $r_1$ ($mM^{-1}s^{-1}$) |
| --- | --- | --- | --- |
| Star Polymer - catechol (20%) | 27.7 | 435 | 12050 |
| Star Polymer - catechol (20%) | 30.7 | 532 | 16332 |
| Star Polymer - catechol (40%) | 70.6 | 1242 | 87685 |
| Star Polymer - catechol (40%) | 79.3 | 1376 | 109117 |

In the exploitation of magnetic features and consequently MRI applications, it is desirable to select a complexing unit that will allow the stable chelation of a paramagnetic compound such as $Gd^{3+}$. For this reason, a catechol complexing unit was investigated. This unit has been extensively studied in biological (marine) applications. However, there have not been any reports of its use in biomedical imaging techniques. Its small size allows a large amount of this chelator to be incorporated into the star polymer structure and inevitably increase the amount of metal present leading to a high relaxivity signal.

In developing novel macromolecular architectures, it was desirable to synthesize aqueous soluble divinyl ethylene oxide fluorene (DVEF) crosslinkers. This crosslinker was reacted with reversible addition fragmentation chain transfer (RAFT) terminated poly(acrylic acid) to successfully form well-defined water soluble star polymers. As a result, divinyl ethylene oxide fluorene poly(acrylic acid) (DVEF PAA) star polymers possessed narrow polydisperities and high molecular weights. The resulting conformation and environment of the chromophore in the star polymeric architectures were then probed by UV-Vis absorption and photoluminescence (PL) measurements. The star polymers from linear RAFT terminated poly(acrylic acid) with incorporated DVEF displayed an absorption and emission wavelength of 340 nm and 376 nm, respectively, with the DVEF monomer emitting at 367 nm. An increase in the PL intensity of the emission spectra of the star polymer architectures in contrast to the monomer was also observed.

To insure optimum water solubility, relatively short poly(ethylene glycol) (PEG) chains were attached to the fluorescent star polymers. Amine terminated tetraethylene glycol units were synthesized through a Mitsonobu reaction. It was then possible to react the terminal amine of the PEG chain with the acrylic acid units through activation of the carboxylic acids using N-methylmorpholine (NMM) and isobutyl chloroformate in dimethylformamide (DMF) at 0° C. Through the incorporation of between 20-40% PEG, we were able to significantly increase the versatility of the polymer allowing for solubility in a number of different solvents including but not limited to water, methanol, and DMF.

To minimize since catechol incompatibility with living free radical polymerization techniques, an acetonide protected catechol unit that could be easily deprotected after incorporation into the polymer chain was selected. The acetonide protected catechol unit was attached to the water soluble star polymers through the same activated carboxylic acid reaction that was successful for incorporation of the PEG chains. This reaction was extremely successful providing a yield of ~95%. Deprotection of the catechol unit was straightforward in aqueous solvent systems through the use of acids such as HCl.

For the chelation of gadolinium, the deprotected catechol containing star polymers were dissolved in water. A solution of gadolinium chloride in water was slowly added to the star polymer solution at room temperature. After successful attachment, the gadolinium containing star polymer solution was dialyzed in 25000 molecular weight cutoff tubing against water for 7 days. $Eu^{3+}$ was also successfully complexed to the star polymers using the same method as the $Gd^{3+}$ incorporation.

C. STAR POLYMERS

In one aspect, the invention relates to star polymers bearing at least one chelating moiety. The disclosed star polymers can be used to prepare the disclosed bimodal contrast agents. In a further aspect, a star polymer comprises a polymeric body having a core with a site-isolated chromophore and a plurality of polymer chains emanating from the core; and at least one chelating moiety bonded to at least one polymer chain. In a further aspect, the polymer is water-soluble.

In a further aspect, the polymer is a water-soluble copolymer of styrene and acrylate; wherein the chromophore is a fluorophore, having a structure represented by a formula:

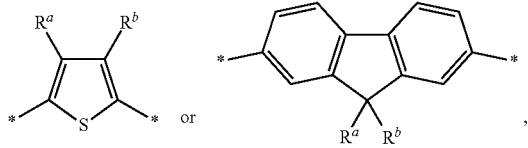

wherein each $R^a$ and $R^b$ is independently selected from hydrogen, alkyl, and polyalkoxyl; and wherein the chelating moiety has a structure represented by a formula:

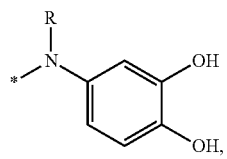

wherein R is hydrogen or alkyl.

1. Polymers

In one aspect, the polymer is olefin-based. For example, the polymer backbone is derived from one or more olefin monomers, including alkyl acrylates, alkyl methacrylates, α-olefins, styrene, and the like. In a further aspect, the polymer is a copolymer of styrene. In a further aspect, the polymer is acrylate-based. In a further aspect, the polymer is a copolymer of acrylate.

2. Size

In one aspect, a star polymer can be provided having a particle size of from about 10 nm to about 100 nm. For example, the particle size can be from about 50 nm to about 100 nm, from about 10 nm to about 50 nm, from about 25 nm to about 75 nm, from about 75 nm to about 100 nm, from about 10 nm to about 50 nm, from about 10 nm to about 75 nm, or from about 25 nm to about 100 nm.

3. Molecular Weight

In one aspect, a star polymer can be provided having a molecular weight of from about 1,000 to about 20,000 g/mol, for example, from about 5,000 to about 15,000, from about 5,000 to about 10,000, from about 1,000 to about 10,000, from about 6,000 to about 12,000, from about 6,000 to about 9,000, or from about 7,000 to about 9,000. In a further aspect, the polymer has a molecular weight ($M_w$) of from about 1.2 to about 9 kg/mol. In a further aspect, the polymer has a molecular weight ($M_w$) of from about 7.2 to about 9.3 kg/mol.

4. Polydispersity

In one aspect, the polymer has a polydispersity (PD) or polydispersity index (PDI) from about 1 to about 3. For example, the PDI can be from about 1 to about 3, from about 1 to about 3, from about 1 to about 2, from about 1 to about 1.8, from about 1 to about 1.6, from about 1 to about 1.4, or from about 1 to about 1.2. In a further aspect, the polymer has a polydispersity index of no more than about 1.6. In a further aspect, the polymer has a polydispersity index of no more than about 1.1. In a further aspect, the polymer has a molecular weight ($M_w$) of about 9 kg/mol and a polydispersity index of no more than about 1.1.

5. Chromophore

In one aspect, the polymer comprises a chromophore. In a further aspect, the chromophore is site-isolated within the star polymer. In a further aspect, the chromophore is a functionalized chromophore and acts as the single branch point within the interior of the star polymer. It is contemplated that any chromophore that can be functionalized to react with the monomers during preparation of the disclosed polymers can be employed. It is alternatively contemplated that any chromophore that can be functionalized to react with the polymer after preparation can be employed to form, for example, a pendant group.

In a further aspect, the chromophore is a fluorophore. In a further aspect, the fluorophore has a structure represented by a formula:

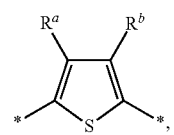

wherein each $R^a$ and $R^b$ is independently selected from hydrogen and alkyl. In a further aspect, the fluorophore has a structure represented by a formula:

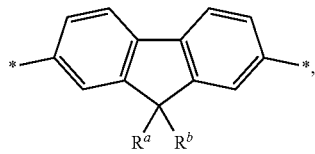

wherein each $R^a$ and $R^b$ is independently selected from hydrogen, alkyl, and polyalkoxyl.

6. Chelating Moiety

In one aspect, the polymer comprises a chelating moiety. It is contemplated that any chromophore that can be functionalized to react with the polymer after preparation can be employed to form, for example, a pendant group. Suitable chelating moieties include DOTA functionalities and catechol functionalities. In a further aspect, the star polymers can further comprise at least one metal chelated by the at least one chelating moiety. In a further aspect, the metal is selected from $Gd^{3+}$ and $Eu^{3+}$.

In a further aspect, the chelating moiety is a catechol-bearing moiety. In a further aspect, the chelating moiety has a structure represented by a formula:

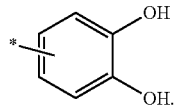

In a further aspect, the chelating moiety has a structure represented by a formula:

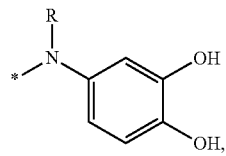

wherein R is hydrogen or alkyl.

In a further aspect, a catechol-based chelating moiety can be prepared according to methods disclosed in Eur. Pat. Appl. (1989), EP 342423 A2 19891123 and/or Cole E. R.; Crank G.; Minh H. T. H., An Improved Method for the Synthesis of 2,2-Disubstituted and 2-Monosubstituted 1,3-Benzodioxoles. *Australian Journal of Chemistry* 1980, 33, 675-680. Both references are incorporated herein for the synthesis of catechol analogues.

7. Dendritic Molecular Transporters

In one aspect, the disclosed star polymers can be provided in combination with one or more covalently bonded dendritic molecular transporter moiety. Such dendritic molecular transporter moieties are disclosed in United States Patent Application Publication No. 2008/0221043

D. BIMODAL CONTRAST AGENT

In one aspect, the invention relates to bimodal contrast agents that can be derived from the disclosed star polymers.

In a further aspect, a bimodal contrast agent comprises a polymeric body having having a core and a plurality of polymer chains emanating from the core; at least one chromophore within the body; at least one chelating moiety bonded to at least one polymer chain; and at least one metal chelated by the at least one chelating moiety. In a further aspect, the agent is water-soluble.

In a further aspect, the polymer is olefin-based. In a further aspect, the polymer is a copolymer of styrene. In a further aspect, the polymer is acrylate-based. In a further aspect, the polymer is a copolymer of acrylate. In a further aspect, the polymer has a molecular weight ($M_w$) of from about 1.2 to about 9 kg/mol. In a further aspect, the polymer has a polydispersity index of no more than about 1.6. In a further aspect, the polymer has a molecular weight ($M_w$) of from about 7.2 to about 9.3 kg/mol. In a further aspect, the polymer has a polydispersity index of no more than about 1.1. In a further aspect, the polymer has a molecular weight ($M_w$) of about 9 kg/mol and a polydispersity index of no more than about 1.1.

In one aspect, the chromophore is a fluorophore. In a further aspect, the fluorophore has a structure represented by a formula:

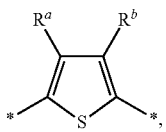

wherein each $R^a$ and $R^b$ is independently selected from hydrogen and alkyl. In a further aspect, fluorophore has a structure represented by a formula:

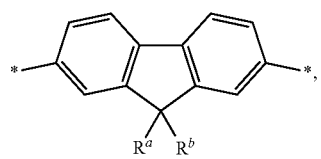

wherein each $R^a$ and $R^b$ is independently selected from hydrogen, alkyl, and polyalkoxyl.

In one aspect, the chelating moiety is a catechol-bearing moiety. In a further aspect, the chelating moiety has a structure represented by a formula:

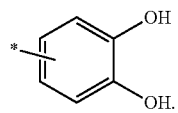

In a further aspect, the chelating moiety has a structure represented by a formula:

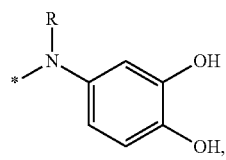

wherein R is hydrogen or alkyl. In a further aspect, the metal is selected from $Gd^{3+}$ and $Eu^{3+}$.

In one aspect, the agent is water-soluble, wherein the polymer is a copolymer of styrene and methyl acrylate; wherein the chromophore is a fluorophore, having a structure represented by a formula:

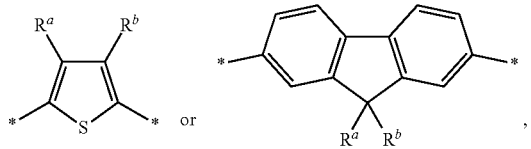

wherein each $R^a$ and $R^b$ is independently selected from hydrogen, alkyl, and polyalkoxyl; wherein the chelating moiety has a structure represented by a formula:

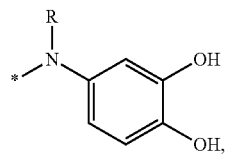

wherein R is hydrogen or alkyl; and wherein the metal is selected from $Gd^{3+}$ and $Eu^{3+}$.

In a further aspect, the agent further comprises at least one covalently bonded dendritic molecular transporter moiety.

E. METHODS OF MAKING

The disclosed polymers and agents can, in various aspects, be prepared according to the methods disclosed herein.

1. Making Star Polymers

In one aspect, a method of making a star polymer comprises the step of introducing at least one chelating moiety into the polymer. In a further aspect, the polymer is water-soluble. In a further aspect, the polymer is olefin-based. In a further aspect, the polymer is a copolymer of styrene. In a further aspect, the polymer is acrylate-based. In a further aspect, the polymer is a copolymer of acrylate. In a further aspect, the chelating moiety is a catechol-bearing moiety. In one aspect, the star polymer comprises a polymeric body having a core with a site-isolated chromophore and a plurality of polymer chains emanating from the core.

In a further aspect, the at least one catechol-bearing moiety is introduced into at least one polymer chain of the polymer. In a further aspect, the chelating moiety has a structure represented by a formula:

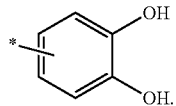

In a further aspect, the chelating moiety has a structure represented by a formula:

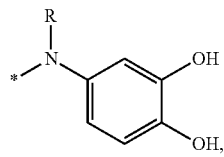

wherein R is hydrogen or alkyl.

In a further aspect, the chelating moiety is introduced by hydrolysis of an acetal or ketal. In a further aspect, the chelating moiety is introduced by hydrolysis of a structure represented by a formula:

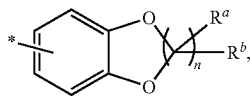

wherein n is 1 or 2, and wherein each $R^a$ and $R^b$ is independently selected from hydrogen and alkyl. In a further aspect, the chelating moiety is introduced by hydrolysis of a structure represented by a formula:

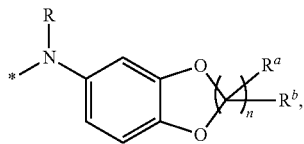

wherein R is hydrogen or alkyl, wherein n is 1 or 2, and wherein each $R^a$ and $R^b$ is independently selected from hydrogen and alkyl.

In a further aspect, the polymer is a water-soluble copolymer of styrene and methyl acrylate; wherein the chromophore is a fluorophore, having a structure represented by a formula:

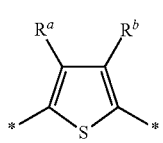 or 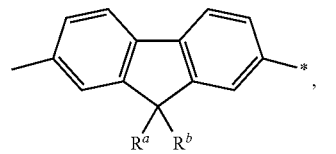

wherein each $R^a$ and $R^b$ is independently selected from hydrogen, alkyl, and polyalkoxyl; wherein the chelating moiety has a structure represented by a formula:

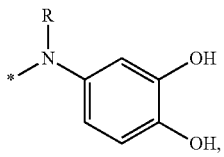

wherein R is hydrogen or alkyl; and wherein the chelating moiety is introduced by hydrolysis of a structure represented by a formula:

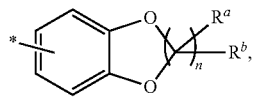

wherein n is 1 or 2, and wherein each $R^a$ and $R^b$ is independently selected from hydrogen and alkyl.

In a further aspect, the method further comprises covalently bonding at least one dendritic molecular transporter moiety.

In a further aspect, the method further comprises the step of chelating at least one metal with the at least one chelating moiety. The metal can be, for example, selected from $Gd^{3+}$ and $Eu^{3+}$.

In a further aspect, the method further comprises the step of conjugating one or more polyoxyalkyleneamine (e.g., Jeffamine®) residues onto the polymer. Conjugation can, for example, be accomplished by treatment with a suitable conjugating agent, such as isobutyl chloroformate.

2. Making Bimodal Contrast Agents

In one aspect, a method of making a bimodal contrast agent comprising the steps of providing a star polymer comprising a polymeric body having a core with a site-isolated chromophore and a plurality of polymer chains emanating from the core; and at least one chelating moiety bonded to at least one polymer chain, and chelating at least one metal with the at least one chelating moiety. In a further aspect, the polymer is water-soluble. In a further aspect, the polymer is olefin-based. In a further aspect, the polymer is a copolymer of styrene. In a further aspect, the polymer is acrylate-based. In a further aspect, the polymer is a copolymer of acrylate.

In one aspect, the chelating moiety is a catechol-bearing moiety. In a further aspect, the at least one catechol-bearing moiety is introduced into at least one polymer chain of the polymer. In a further aspect, the chelating moiety has a structure represented by a formula:

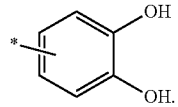

In a further aspect, the chelating moiety has a structure represented by a formula:

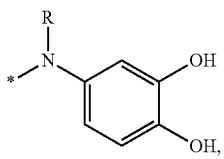

wherein R is hydrogen or alkyl.

In one aspect, the chelating moiety is introduced by hydrolysis of an acetal or ketal.

In a further aspect, the chelating moiety is introduced by hydrolysis of a structure represented by a formula:

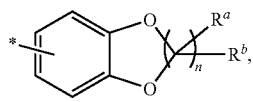

wherein n is 1 or 2, and wherein each $R^a$ and $R^b$ is independently selected from hydrogen and alkyl. In a further aspect, the chelating moiety is introduced by hydrolysis of a structure represented by a formula:

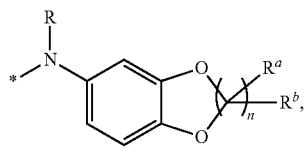

wherein R is hydrogen or alkyl, wherein n is 1 or 2, and wherein each $R^a$ and $R^b$ is independently selected from hydrogen and alkyl.

In a further aspect, the polymer is a water-soluble copolymer of styrene and methyl acrylate; wherein the chromophore is a fluorophore, having a structure represented by a formula:

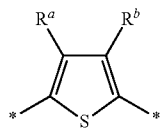 or 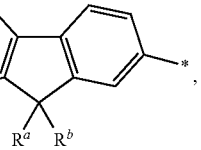

wherein each $R^a$ and $R^b$ is independently selected from hydrogen, alkyl, and polyalkoxyl; wherein the chelating moiety has a structure represented by a formula:

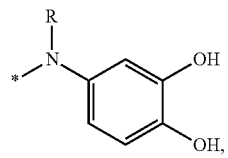

wherein R is hydrogen or alkyl; wherein the chelating moiety is introduced by hydrolysis of a structure represented by a formula:

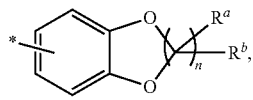

wherein n is 1 or 2, and wherein each $R^a$ and $R^b$ is independently selected from hydrogen and alkyl; and wherein the metal is selected from $Gd^{3+}$ and $Eu^{3+}$.

In a further aspect, the method further comprises covalently bonding at least one dendritic molecular transporter moiety.

F. METHODS OF USING

It is contemplated that the disclosed star polymers can be used in various applications, including conventional applications of known star polymers and bimodal contrast agents. The disclosed bimodal contrast agents, however, have further usefulness in imaging methods. In one aspect, an imaging method comprises the steps of administering into a cell a diagnostically effective amount of a bimodal contrast agent comprising a polymeric body having a core and a plurality of polymer chains emanating from the core; at least one chromophore within the body; at least one chelating moiety bonded to at least one polymer chain; and at least one metal chelated by the at least one chelating moiety, and imaging the cell with one or both of a Magnetic Resonance Imaging apparatus or a chromatographic detector. In a further aspect, an imaging method comprising the steps of administering into soft tissue of a subject a diagnostically effective amount of a bimodal contrast agent comprising a polymeric body having a core and a plurality of polymer chains emanating from the core; at least one chromophore within the body; at least one chelating moiety bonded to at least one polymer chain; and at least one metal chelated by the at least one chelating moiety, and imaging the soft tissue of the subject with one or both of a Magnetic Resonance Imaging apparatus or a chromatographic detector. In one aspect, the subject is a mammal, for example, a human.

In one aspect, the polymer is a water-soluble copolymer of styrene and methyl acrylate; wherein the chromophore is a fluorophore, having a structure represented by a formula:

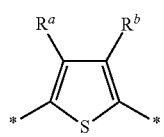 or 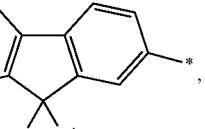

wherein each $R^a$ and $R^b$ is independently selected from hydrogen, alkyl, and polyalkoxyl; wherein the chelating moiety has a structure represented by a formula:

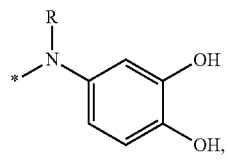

wherein R is hydrogen or alkyl; wherein the chelating moiety is introduced by hydrolysis of a structure represented by a formula:

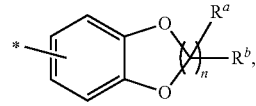

wherein n is 1 or 2, and wherein each $R^a$ and $R^b$ is independently selected from hydrogen and alkyl; and wherein the metal is selected from $Gd^{3+}$ and $Eu^{3+}$.

In one aspect, the polymer is a water-soluble copolymer of styrene and methyl acrylate; wherein the chromophore is a fluorophore, having a structure represented by a formula:

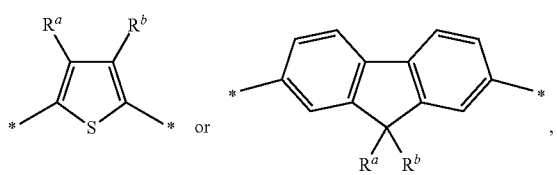

wherein each $R^a$ and $R^b$ is independently selected from hydrogen, alkyl, and polyalkoxyl; wherein the chelating moiety has a structure represented by a formula:

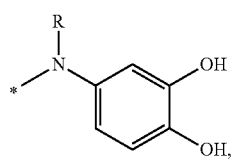

wherein R is hydrogen or alkyl; and wherein the metal is selected from $Gd^{3+}$ and $Eu^{3+}$.

In a further aspect, the agent further comprises at least one covalently bonded dendritic molecular transporter moiety.

The disclosed compositions can be delivered to a cell or a subject by administering a diagnostically effective amount and imaging with one or both of a Magnetic Resonance Imaging apparatus or a chromatographic detector. Examples of excised mouse tissue dosed with disclosed imaging agents are show in FIGS. 12-16. Claimed compositions were used in the upper image (top, white color) of each Figure, whereas conventional compositions were used in the lower image (bottom, red color). As shown, use of the claimed compositions exhibits superior imaging results over use of conventional compostions.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Materials.

2,7-Dibromofluorene (Aldrich, 97%), tetrabutylammonium bromide (Aldrich, 99%), 1-bromo-2,2-methoxyethoxy-ethane (Acros, 90%), vinyltrimethylsilane (Acros, 97%), triphenylphosphine (PPh3, Aldrich, 99%), palladium acetate (Pd(OAc)2, Aldrich, 98%), triethylamine (NEt3, Aldrich, 99.5%), 9,9'-dihexyl-2,7-dibromofluorene (Aldrich, 97%), styrene (Acros, stabilized), acrylic acid (Acros, 99.5%), and azobis(isobutyronitrile) (AIBN, Aldrich, 98%) were used as received. 4-methylmorpholine, isobutyl chloroformate, gadolinium chloride, and europium chloride were used as received. SnakeSkin pleated dialysis tubing was obtained from Pierce Biotechnology, Inc. (Rockford, Ill.). 2,2,5-Trimethyl-2-(1-phenylethoxy)-4-phenyl-3-azahexane (Ralkoxyamine), 4-cyanopentanoic acid dithiobenzoate, and 2,5-dibromo-3-hexylthiophene were prepared as described previously. All solvents were commercially available and used as received.

Techniques.

Analytical thin layer chromatography (TLC) was carried out on commercial Merck plates coated with silica gel GF254 (0.24 mm). Column chromatography was carried out with Merck silica gel, 230-400 mesh. $^1H$ NMR and $^{13}C$ spectra (δ, ppm) were recorded on a 400 MHz FT-NMR spectrometer at ambient temperature. All spectra were recorded in $CDCl_3$, MeOD, or $D_2O$ and the resonances were measured relative to residual solvent. Weight-average ($M_w$) molecular weights relative to linear polystyrene and polydispersity indexes ($PDI=M_w/M_n$) were determined by gel permeation chromatography (GPC) at ambient temperature using tetrahydrofuran (THF) as solvent (1.0 mL/min), a set of $10^2$, $10^3$, $10^5$, $10^6$ Å Styragel 5 μm columns, a Waters 410 differential refractometer, and Millenium Empower 2 software. Particle size and absolute molecular weights were determined by dynamic light scattering (DLS) and static light scattering (SLS), respectively, on a Zetasizer Nano Series instrument at 25° C. with a CGS-3 compact goniometer system by Malvern Instruments equipped with a vertically polarized 35 mW He—Ne 633 laser with polyacrylate based samples dissolved in methanol. All samples were dissolved overnight, filtered through a 0.45 μm filter, and run at a fixed 90° angle with the light wavelength at 690 nm.

The values of refractive index increment (dn/dc) for star polymers were measured in THF at 25° C. by using a refractometer. UV-Visible (UV-Vis) absorption spectra were obtained with a Varian Cary 50 spectrophotometer with samples in methanol. Photoluminescence spectra were taken on an ISS PCI photon counting spectrofluorometer in their respective solvents. Fluorescence quantum yields ($Φ_f$) were determined relative to 9,10-diphenylanthracene in cyclohexane ($Φ_f$=0.9) as the standard. Low field (0.5 T) T1 determinations were made using a 0.5 T NMR scanner operating at 40° C., using a standard inversion recovery sequence and employed six different concentrations of $Gd^{3+}$ labeled star polymers. Samples were acquired in triplicate. Relaxivity measurements ($r_1$) were determined from T1 values using a plot of the measured values of 1/T1 versus Gd concentration (mM). Linear fits of the resulting plots ($r_2$>0.99) subsequently gave $r_1$ values.

The values of refractive index increment (dn/dc) for star polymers were measured in THF at 25° C. by using a refractometer. UV-vis absorption spectra were obtained with a Varian Cary 50 spectrophotometer, and polystyrene-based architectures were analyzed in cyclohexane whereas polyacrylate-based samples were analyzed in methanol.

Photoluminescence spectra were taken on an ISS PCI photon counting spectrofluorometer in their respective solvents. Fluorescence quantum yields ($Φ_f$) were determined relative to 9,10-diphenylanthracene in cyclohexane (Φ) 0.9) as the standard. A Thermo Finnigan LCQ Deca XP quadrapole ion trap mass spectrometer (Thermo Finnigan, San Jose, Calif.) equipped with an atmospheric pressure chemical infusion (APCI) ionization source operating in electrospray mode was used in positive ion mode to acquire mass spectrum data.

1. Synthesis of 2,7-dibromo-9,9-bis(2-(2-methoxyethoxy)ethyl)fluorene, 2

2,7-Dibromofluorene (10.0 g, 30.9 mmol) was added to a mixture of aqueous potassium hydroxide (175 mL, 50%), tetrabutylammonium bromide (2.1 g, 6.5 mmol), and 1-bromo-2-(2-methoxyethoxy)ethane (28.4 g, 155 mmol) at 75° C. After 30 min, the mixture was cooled to room temperature and extracted with dichloromethane. The organic layers were washed successively with water, aqueous HCl (1 M), water, and brine, dried over magnesium sulfate, and concentrated. The product was purified by flash column chromatography (5:1 hexanes/ethyl acetate) to give a yellow oil (8.3 g, 83%). $^1$H NMR (CDCl$_3$): δ (ppm) 7.45-7.6 (m, 6H, ArH), 3.3 (s, 6H, OCH3), 3.2 (s, 4H, OCH2), 2.75 (t, 4H, OCH2, J) 7.1 Hz), 2.35 (t, 4H, OCH2, J) 7.1 Hz), 1.55 (s, 4H, CH2CH3). $^{13}$C NMR (CDCl$_3$): δ 149.4, 139.88, 136.93, 125.77, 120.68, 119.77, 113.49, 69.83, 66.96, 68.99, 58.91, 50.86, 39.72, 17.23. ESI-MS (CH3CN, positive): m/z 546 (M$^+$+H3O, 100%), 544 (M$^+$+O, 49%), 529 (M$^+$+H, 48%).

2. Synthesis of 9,9-Bis(2-(2-methoxyethoxy)ethyl)-2,7-divinylfluorene, DVEF, 3

Vinyltrimethylsilane (11.4 g, 114 mmol), NEt$_3$ (12.5 g, 126 mmol), PPh3 (0.97 g, 3.7 mmol), and Pd(OAc)$_2$ (0.42 g, 1.9 mmol) were dissolved in 20 mL of anhydrous dimethylformamide (DMF) and added to a solution of 2 in 5 mL of DMF (6.0 g, 11 mmol). The mixture was purged with N2 and heated at 100° C. in a sealed flask. After 1 h, additional vinyltrimethylsilane (2.85 g, 28.4 mmol), Et$_3$N (6.25 g, 61.7 mmol), PPh3 (0.485 g, 1.85 mmol), and Pd(OAc)$_2$ (0.21 g, 0.94 mmol) were dissolved in 5 mL of DMF and added via syringe to the solution. The reaction flask was then purged with N$_2$ three times. After 2 h, another equivalent of vinyltrimethylsilane (2.85 g, 28.4 mmol), Et$_3$N (6.25 g, 61.7 mmol), PPh3 (0.485 g, 1.85 mmol), and Pd(OAc)$_2$ (0.21 g, 0.94 mmol) in 5 mL of DMF were added via syringe to the solution. The reaction flask was again purged with N$_2$ three times. After 24 h, the solution was allowed to cool to room temperature, diluted in dichloromethane, and filtered. The solution was then washed with water (3×200 mL). The organic layers were collected, dried over magnesium sulfate, and concentrated. The residue was purified by column chromatography (5:1 hexanes/ethyl acetate) to yield a yellow oil which crystallized at room temperature. The purified product was dissolved in 10 mL of 1.0 M tetrabutylammonium fluoride (TBAF) in THF and heated to 80° C. for 24 h. The reaction mixture was diluted in CH$_2$Cl$_2$ and washed with water (3×100 mL), and the organic layers were collected and concentrated in vacuo. The product was purified by column chromatography (2:1 hexanes/ethyl acetate) to give a yellow oil (3.81 g, 90.7%). $^1$H NMR (CDCl$_3$): δ (ppm) 7.4-7.7 (m, 6H, ArH), 6.80 (dd, 1H, CH2CH, J) 17.6, J) 10.5 Hz), 5.82 (d, 1H, CH, J) 16.7 Hz), 5.25 (d, 1H, CH, J) 10.9 Hz), 3.3 (m, 6H, OCH3), 3.2 (m, 4H, OCH2), 2.75 (t, 4H, OCH2, J) 6.1 Hz), 2.45 (t, 4H, OCH2, J) 6.1 Hz), 1.6 (s, 6H, CH3CH2). $^{13}$CNMR (CDCl$_3$): δ 149.40, 139.88, 136.93, 125.77, 120.68, 119.77, 113.49, 69.83, 71.95, 66.96, 58.91, 50.86, 39.72, 17.23. ESI-MS (CH3CN, positive): m/z=423 (M$^+$+H, 100%), 440 (M$^+$+H2O, 96%).

3. Synthesis of 9,9-Dihexyl-2,7-divinylfluorene, DVHF, 4

Vinyltrimethylsilane (14.3 g, 142 mmol), Et$_3$N (15.7 g, 155 mmol), PPh$_3$ (1.22 g, 4.6 mmol), and Pd(OAc)$_2$ (0.52 g, 2.3 mmol) were dissolved in 30 mL of anhydrous DMF and added to a solution of 9,9-dihexyl-2,7-dibromofluorene in 5 mL of DMF (7.0 g, 14 mmol). The mixture was purged with N$_2$ and heated at 100° C. in a sealed flask. After 1 h, additional vinyltrimethylsilane (3.56 g, 35.5 mmol), Et$_3$N (7.82 g, 77.3 mmol), PPh$_3$ (0.61 g, 2.3 mmol), and Pd(OAc)$_2$ (0.26 g, 1.2 mmol) were dissolved in 5 mL of DMF and added via syringe to the solution. The reaction flask was then purged with N$_2$ three times. After 2 h, another equivalent of vinyltrimethylsilane (3.56 g, 35.5 mmol), Et$_3$N (7.82 g, 77.3 mmol), PPh3 (1.22 g, 4.6 mmol), and Pd(OAc)$_2$ (0.52 g, 2.3 mmol) were dissolved in 5 mL of DMF and added via syringe to the solution. The reaction flask was again purged with N2 three times. After 24 h, the solution was allowed to cool to room temperature, diluted in dichloromethane, and filtered. The solution was then washed with water (3×200 mL). The organic layers were collected, dried over magnesium sulfate, and concentrated. The residue was purified by column chromatography (5:1 hexanes/ethyl acetate). The purified product was dissolved in 10 mL of 1.0 M TBAF in THF and heated to 80° C. for 24 h. The reaction mixture was diluted in CH$_2$Cl$_2$ and washed with water (3×100 mL), and the organic layers were collected and concentrated in vacuo. The product was purified by column chromatography (2:1 hexanes/ethyl acetate) to give a colorless oil (4.95 g, 70.7%). $^1$H NMR (CDCl$_3$): δ (ppm) 7.32 (m, 6H ArH), 6.81 (dd, 1H, CH2CH, J) 17.6, J) 10.9 Hz), 5.85 (d, 1H, CH, J) 17.6 Hz), 5.28 (d, 1H, CH, J) 10.7 Hz), 1.9 (m, 4H, CH2), 0.95 (m, 16H, CH2), 0.70 (t, 6H, CH2CH3, J) 6.9 Hz). $^{13}$C NMR (CDCl$_3$): δ 150.1, 142.1, 139.5, 138.5, 129.3, 127.2, 123.2, 115.2, 54.0, 44.2, 30.1, 28.7, 23.2, 22.1, 14.8. ESI-MS (CH3CN, positive): m/z=403 (M$^+$+OH, 100%).

4. Synthesis OF 3-Hexyl-2,5-divinylthiophene, DVHT, 5

Vinyltrimethylsilane (22.0 g, 222 mmol), Et$_3$N (48.8 g, 482 mmol), PPh3 (3.79 g, 14.5 mmol), and Pd(OAc)$_2$ (1.63 g, 7.27 mmol) were dissolved in 40 mL of DMF and added to a solution of 2,5-dibromo3-hexylthiophene in DMF (14.5 g, 44.3 mmol). The mixture was purged with N$_2$ and heated at 100° C. in a sealed flask. After 1 h, additional vinyltrimethylsilane (11.0 g, 111 mmol), Et$_3$N (24.4 g, 241 mmol), PPh$_3$ (1.9 g, 7.3 mmol), and Pd(OAc)$_2$ (0.82 g, 3.6 mmol) were dissolved in 20 mL of DMF and added via syringe to the solution. The reaction flask was then purged with N$_2$ three times. After 2 h, another equivalent of vinyltrimethylsilane (11.0 g, 111 mmol), Et$_3$N (24.4 g, 241 mmol), PPh$_3$ (1.9 g, 7.3 mmol), and Pd(OAc)$_2$ (0.82 g, 3.6 mmol) in 20 mL of DMF were added via syringe to the solution. The reaction flask was again purged with N$_2$ three times. After 24 h, the solution was allowed to cool to room temperature, diluted in dichloromethane, and filtered. The solution was then washed with water (3×200 mL). The organic layers were collected, dried over magnesium sulfate, and concentrated. The residue was purified by column chromatography (20:1 hexanes/ethyl acetate) to yield a dark brown oil. The purified product was dissolved in 10 mL of 1.0 M TBAF in THF and heated to 80° C. for 24 h. The reaction mixture was diluted in CH$_2$Cl$_2$ and washed with water (3×100 mL), and the organic layers were collected and concentrated in vacuo. The product was purified by column chromatography (2:1 hexanes/ethyl acetate) to give a yellow oil (12.1 g, 83.4%). $^1$H NMR (CDCl$_3$): δ (ppm) 6.86 (m, 1H, ArH), 6.56 (q, 2H, CH2CH), 5.48 (d, 1H, CH, J) 17.1 Hz), 5.08 (d, 1H, CH, J) 10.9 Hz), 2.64 (m, 2H, CH2), 1.57 (m, 8H, CH2), 0.98 (m, 3H, CH2CH3). $^{13}$C NMR (CDCl$_3$): δ 131.05, 129.89, 127.96, 127.12, 124.95, 114.71, 113.21, 32.18, 31.29, 29.17, 28.97, 22.37, 20.56, 13.94. ESI-MS (CH3CN, positive): m/z) 237 (M$^+$+OH, 100%).

5. Macroinitiators. General Procedure for Styrene Polymerization, 6

A mixture of styrene (5.2 g, 50 mmol) and 2,2,5-trimethyl-2-(1-phenylethoxy)-4-phenyl-3-azahexane (0.16 g, 0.5 mmol) was degassed by three freeze/pump/thaw cycles, sealed under argon, and heated at 124° C. for 8 h. The viscous reaction mixture was then allowed to cool, dissolved in dichloromethane (10 mL), and precipitated into methanol (500 mL). The white powder was filtered and then dried in vacuo to yield the R-hydridoalkoxyamineterminated polystyrene (4.36 g, 83.8%, Mw) 9000, PDI) 1.17).[32] 1H NMR (CDCl$_3$): δ (ppm) 6.32-7.4 (br m), 1.28-2.12 (br m).

6. General Procedure for Acrylate Polymerization, 7

A mixture of acrylic acid (3.6 g, 50 mmol), 4-cyanopentanoic acid dithiobenzoate (0.14 g, 0.59 mmol), and azobis (isobutyronitrile) (AIBN) (0.0 16 g, 0.100 mmol) was degassed by three freeze/pump/thaw cycles, sealed under argon, and heated at 70° C. for 16 h. The viscous reaction mixture was then allowed to cool, dissolved in methanol (10 mL), and precipitated once into ethyl acetate (500 mL). The polymer was filtered and then dried in vacuo to give the desired polymer (3.10 g, 86.1%, Mw) 7700, PDI) 1.1 1). $^1$H NMR (CDCl$_3$): δ (ppm) 5.03 (br s, COOH), 4.35 (br s, CH), 2.68 (br s, CH2), 2.42 (br s, CH2), 1.95 (br s, CH2), 1.50-1.85 (br m, CH2).

7. General Procedure for Formation of Hexylfluorene Star Polymers, 10 and 11

A mixture of the polymeric macroinitiator, 6 (2.0 g, 0.29 mmol, Mw) 7300, PDI) 1.17), styrene (0.2791 g, 2.20 mmol), and 4 (0.346 g, 0.88 mmol) was dissolved in chlorobenzene (1.86 mL), degassed by four freeze/pump/thaw cycles, and sealed under argon. The polymerization mixture was then stirred at 124° C. for 16 h and allowed to cool, and the star polymer, 11, was obtained after precipitation into methanol (2.3 g, 84%, Mw) 190 400, PDI) 1.28). $^1$H NMR (CDCl$_3$): δ (ppm) 6.32-7.2 (br m), 1.28-2.12 (br m).

8. General Procedure for Formation of Hexylthiophene Star Polymers, 16 and 17

A mixture of the polymeric macroinitiator, 6 (2.0 g, 0.30 mmol, Mw) 7200, PDI) 1.09), styrene (0.258 g, 2.48 mmol), and 5 (0.916 g, 4.15 mmol) was dissolved in chlorobenzene (2.9 mL), degassed by four freeze/pump/thaw cycles, and sealed under argon. The polymerization mixture was then stirred at 124° C. for 16 h and allowed to cool, and the star polymer, 16, was obtained after precipitation into methanol (3.1 g, 90%, Mw) 49400, PDI) 1.58). $^1$H NMR (CDCl$_3$): δ (ppm) 6.32-7.2 (br m), 0.81-2.12 (br m).

9. General Procedure for Formation of EO Fluorene Star Polymers, 20, 21, 22, and 23

A mixture of the polymeric macroinitiator, 7 (2.0 g, 0.22 mmol, Mw) 7700, PDI) 1.11), 3 (0.668 g, 1.55 mmol), and AIBN (0.43 mg, 0.03 mmol) was dissolved in 2% H2O in THF (6.0 mL), degassed by four freeze/pump/thaw cycles, and sealed under argon. The polymerization mixture was then stirred at 85° C. for 48 h and allowed to cool, and the star polymer, 23, was obtained after precipitation using ethyl acetate followed by dialysis against methanol (1.9 g, 71%, Mw) δ 500, PDI) 1.32). $^1$H NMR (CDCl$_3$): δ (ppm) 7.10-7.28 (br m, ArH), 5.03 (br s, CH), 4.35 (br s, CH2), 2.68 (br s, CH2), 2.42 (br s, CH2), 1.95 (br s, CH2), 1.50-1.85 (br m, CH2).

10. General Procedure for 3-Butenylamine Attachment to Acetonide Protected Catechol Triethylene Glycol Poly(Acrylic Acid) Ethylene Oxide Fluorene Star Polymers, 24

A solution of 29 (0.04 g, 0.04 mmol) in 5 mL of dry DMF was injected into a flame dried 3-neck round bottom flask and stirred over an ice-water bath. 4-methylmorpholine (0.004 g, 0.04 mmol) and isobutyl chloroformate (0.005 g, 0.05 mmol) were added to the stirring solution. After 1 h, 3-butenylamine hydrochloride (0.005 g, 0.04 mmol) was added to the solution and stirred overnight, subsequently transferred to dialysis tubing (MWCO=25,000), and allowed to dialyze against methanol for 3 days. The solution was then collected and concentrated in vacuo. (0.04 g, 74%, $M_w$=220 000, PDI=1.24). $^1$H NMR (MeOD): δ (ppm) 7.60-7.95 (br, m), 3.20-3.85 (br, m), 2.10-2.55 (br, m), 1.35-2.05 (br, m), 1.20-1.30 (br, s).

11. General Procedure for Molecular Transporter Attachment to Acetonide Protected Catechol Triethylene Glycol Poly(Acrylic Acid) Ethylene Oxide Fluorene Star Polymers, 25

Molecular transporter (0.01 g, 0.004 mmol) was added to a solution of 30 (0.04 g, 0.002 mmol) in 0.4 mL of methanol. This mixture was stirred at 33° C. for 48 h, subsequently transferred to dialysis tubing (MWCO=25,000), and allowed to dialyze against methanol for 3 days. The solution was then collected and concentrated in vacuo. (0.01 g, 71%, $M_w$=256 000, PDI=1.22). $^1$H NMR (MeOD): δ (ppm) 7.60-7.95 (br, m), 3.20-3.85 (br, m), 2.10-2.55 (br, m), 1.35-2.05 (br, m), 1.20-1.30 (br, s).

12. General Procedure for Deprotection of Acetonide Protected Catechol Poly(Acrylic Acid) Ethylene Oxide Fluorene Star Polymers, 26

To a stirring solution of 31 (0.01 g, 0.004 mmol) dissolved in 10 mL of water was added 10 mL of 6M HCl. This mixture was allowed to stir for 3 h at ambient temperature and concentrated in vacuo to give a light brown residue. (0.007 g, 70%, $M_w$=255 000, PDI=1.23). $^1$H NMR (MeOD): δ (ppm) 7.60-7.95 (br, m), 3.20-3.85 (br, m), 2.10-2.55 (br, m), 1.35-2.05 (br, m), 1.20-1.30 (br, s).

13. Preparation of Gd-Coordinated Catechol Poly(Acrylic Acid) Ethylene Oxide Fluorene Star Polymers, 27

To a stirred solution of 32 (0.007 g, 0.004 mmol) in deionized water at ambient temperature was added 2 g of GdCl$_3$ in 10 mL of H$_2$O. The reaction mixture was allowed to stir overnight, subsequently transferred to dialysis tubing (MWCO=25,000), and allowed to dialyze against de-ionized water for 7 days. The solution was then collected and concentrated in vacuo. (0.012 g, $M_w$=290 000, PDI=1.21).

14. Preparation of Eu-Coordinated Catechol Poly(Acrylic Acid) Ethylene Oxide Fluorene Star Polymers, 28

To a stirred solution of 32 (0.007 g, 0.004 mmol) in deionized water at ambient temperature was added 1 g of EuCl$_3$ in 10 mL of H$_2$O. The reaction mixture was allowed to stir overnight, subsequently transferred to dialysis tubing (MWCO=25,000), and allowed to dialyze against de-ionized water for 7 days. The solution was then collected and concentrated in vacuo. (0.011 g, 60%, $\Phi_f$=6%, $M_w$=286 000, PDI=1.21).

15. General Procedure for Cyclic RGD Attachment to Acetonide Protected Catechol Triethylene Glycol Poly(Acrylic Acid) Ethylene Oxide Fluorene Star Polymers, 29

Cyclic RGD (0.01 g) was added to a solution of 30 (0.01 g, 0.004 mmol) in 0.5 mL of $H_2O$. The mixture was stirred at stirred at 33° C. for 72 h, subsequently transferred to dialysis tubing (MWCO=25,000), and allowed to dialyze against water for 3 days. The solution was then collected and concentrated in vacuo. (0.01 g, 71%, $M_w$=230 000, PDI=1.23).

16. General Procedure for Formation Triethylene Glycol Poly(Acrylic Acid) Ethylene Oxide Fluorene Star Polymers, 33

A solution of poly(acrylic acid) ethylene oxide star polymer (0.15 g, 0.42 mmol) in 10 mL of dry DMF was injected into a flame dried 3-neck round bottom flask and stirred over an ice-water bath. 4-methylmorpholine (0.08 g, 0.79 mmol) and isobutyl chloroformate (0.13 g, 0.95 mmol) were added to the stirring solution. After 1 h, 3,6,9-trioxadecylamine (0.14 g, 0.85 mmol) was added to the solution and stirred overnight, subsequently transferred to dialysis tubing (MWCO=25,000), and allowed to dialyze against methanol for 2 days. The solution was then collected and concentrated in vacuo. (0.41 g, 81%, Mw=207 000, PDI=1.21). $^1$H NMR (MeOD): δ (ppm) 7.60-7.95 (br, m), 3.20-3.85 (br, m), 2.10-2.55 (br, m), 1.40-2.05 (br, m), 1.20-1.30 (br, s).

17. General Procedure for Formation of Acetonide Protected Catechol Triethylene Glycol Poly(Acrylic Acid) Ethylene Oxide Fluorene Star Polymers, 34

A solution of 33 (0.41 g, 0.002 mmol) in 10 mL of dry DMF was injected into a flame dried 3-neck round bottom flask and stirred over an ice-water bath. 4-methylmorpholine (0.04 g, 0.40 mmol) and isobutyl chloroformate (0.06 g, 0.44 mmol) were added to the stirring solution. After 1 h, 2,2-dimethylbenzo-1,3-dioxol-5-amine (0.07 g, 0.42 mmol) was added to the solution and stirred overnight, subsequently transferred to dialysis tubing (MWCO=25,000), and allowed to dialyze against methanol for 2 days. The solution was then collected and concentrated in vacuo. (0.42 g, 72%, Mw=220 000, PDI=1.24). $^1$H NMR (MeOD): δ (ppm) 7.60-7.95 (br, m), 3.20-3.85 (br, m), 2.10-2.55 (br, m), 1.35-2.05 (br, m), 1.20-1.30 (br, s).

18. General Procedure for Deprotection of Acetonide Protected Catechol Poly(Acrylic Acid) Ethylene Oxide Fluorene Star Polymers, 35

To a stirring solution of 34 (0.42 g, 0.002 mmol) dissolved in 10 mL of water was added 5 mL of 6M HCl. This mixture was allowed to stir for 3 h at ambient temperature and concentrated in vacuo to give a light brown residue. (0.33 g, 79%, Mw=219 000, PDI=1.23). $^1$H NMR (D$_2$O): δ (ppm) 7.60-7.95 (br, m), 3.20-3.85 (br, m), 2.10-2.55 (br, m), 1.35-2.10 (br, m), 1.25-1.30 (br, s).

19. Preparation of Gd-Coordinated Catechol Poly(Acrylic Acid) Ethylene Oxide Fluorene Star Polymers, 36

To a stirred solution of 35 (0.33 g, 0.0013 mmol) in deionized water at ambient temperature was added 2 g of GdCl3 in 10 mL of H2O. The reaction mixture was allowed to stir overnight, subsequently transferred to dialysis tubing (MWCO=25,000), and allowed to dialyze against de-ionized water for 7 days. The solution was then collected and concentrated in vacuo. (0.2 g, 61%, Mw=290 000, PDI=1.21).

20. Preparation of Eu-Coordinated Catechol Poly(Acrylic Acid) Ethylene Oxide Fluorene Star Polymers, 37

To a stirred solution of 35 (0.15 g, 0.0006 mmol) in deionized water at ambient temperature was added 1 g of EuCl$_3$ in 10 mL of H$_2$O. The reaction mixture was allowed to stir overnight, subsequently transferred to dialysis tubing (MWCO=25,000), and allowed to dialyze against de-ionized water for 7 days. The solution was then collected and concentrated in vacuo. (0.09 g, 60%, Mw=275 000, PDI=1.22, $\Phi_f$=7.1%).

21. General Procedure for Formation of Jeffamine® Conjugated Poly(Acrylic Acid) Ethylene Oxide Fluorene Star Polymers, 47

A solution of poly(acrylic acid) ethylene oxide star polymer (PAA DVEF) (0.20 g, 0.85 mmol, $M_w$=69,000 Da (GPC), $M_w$=207,000 Da (SLS), PDI=1.23) in 5 mL of dry DMF was injected into a flame dried 3-neck round bottom flask and stirred over an ice-water bath. N-methylmorpholine (0.12 g, 1.19 mmol) and isobutyl chloroformate (0.17 g, 1.27 mmol) were added to the stirring solution. After 1 h, Jeffamine® M-2070 (2.37 g, 1.19 mmol) was added to the solution and stirred overnight, subsequently transferred to dialysis tubing (MWCO=25,000) and allowed to dialyze against methanol for 2 days. The solution was then collected and concentrated in vacuo. (2.09 g, 81%, $M_w$=1100 kDa (SLS)). DLS: $D_H$=14.8±1.5 nm. $^1$H NMR (D$_2$O): δ (ppm) 7.53-7.98 (br, m), 4.35 (br, s), 4.05 (br, s), 3.51-3.83 (br, m), 2.13-2.61 (br, m), 1.44-1.99 (br, m), 1.18-1.17 (br, d), 0.93 (br s).

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A bimodal contrast agent comprising:
 (a) a polymeric body having a core and a plurality of polymer chains emanating from the core, wherein the polymer is a copolymer of styrene and methyl acrylate;
 (b) at least one chromophore derived from 9,9-Bis(2-(2-methoxyethoxy)ethyl)ethyl)-2,7-divinylfluorene; 9,9-Dihexyl-2,7-divinylfluorene; or 3-Hexyl-2,5-divinylthiophene within the body;
 (c) at least one catechol-bearing chelating moiety bonded to at least one polymer chain; and
 (d) at least one metal chelated by the at least one chelating moiety, wherein the metal is selected from Gd$^{3+}$ and Eu$^{3+}$,
 wherein the agent is water-soluble.
2. The agent of claim 1, wherein the metal is Gd$^{3+}$.
3. The agent of claim 1, wherein the metal is Eu$^{3+}$.
4. The agent of claim 1, wherein the polymer has a molecular weight ($M_w$) of from about 1.2 to about 9 kg/mol.

5. The agent of claim 1, wherein the polymer has a polydispersity index of no more than about 1.6.

6. The agent of claim 1, wherein the polymer has a molecular weight ($M_w$) of from about 7.2 to about 9.3 kg/mol.

7. The agent of claim 1, wherein the polymer has a polydispersity index of no more than about 1.1.

8. The agent of claim 1, wherein the polymer has a molecular weight ($M_w$) of about 9 kg/mol and a polydispersity index of no more than about 1.1.

9. The agent of claim 1, further comprising at least one covalently bonded dendritic molecular transporter moiety.

10. The agent of claim 1, further comprising one or more polyoxyalkylenamine residues bonded to a polymer chain.

* * * * *